US007785632B2

(12) United States Patent
Mousa et al.

(10) Patent No.: US 7,785,632 B2
(45) Date of Patent: Aug. 31, 2010

(54) THYROID HORMONE ANALOGS AND METHODS OF USE

(75) Inventors: Shaker A. Mousa, Wynantskill, NY (US); Faith B. Davis, West Sand Lake, NY (US); Paul J. Davis, West Sand Lake, NY (US)

(73) Assignees: Ordway Research Institute, Inc., Albany, NY (US); Albany College of Pharmacy, Albany, NY (US)

( * ) Notice: Subject to any disclaimer, the term of this patent is extended or adjusted under 35 U.S.C. 154(b) by 493 days.

(21) Appl. No.: 10/943,072

(22) Filed: Sep. 15, 2004

(65) Prior Publication Data
US 2005/0124862 A1 Jun. 9, 2005

Related U.S. Application Data

(60) Provisional application No. 60/502,721, filed on Sep. 15, 2003.

(51) Int. Cl.
*A61K 9/14* (2006.01)
*A61K 9/50* (2006.01)

(52) U.S. Cl. ...................... 424/501; 424/489
(58) Field of Classification Search ........... 424/489–502
See application file for complete search history.

(56) References Cited

U.S. PATENT DOCUMENTS

| 3,625,214 A |   | 12/1971 | Higuchi ............... 128/260 |
| 4,205,058 A | * | 5/1980 | Wagner et al. ......... 436/500 |
| 4,650,751 A | * | 3/1987 | Siegel et al. .......... 435/7.1 |
| 4,789,734 A |   | 12/1988 | Pierschbacher ......... 530/395 |
| 4,801,504 A | * | 1/1989 | Burdick et al. ......... 428/403 |
| 4,801,575 A |   | 1/1989 | Pardridge ............. 514/4 |
| 4,906,474 A |   | 3/1990 | Langer et al. ......... 424/428 |
| 4,925,673 A |   | 5/1990 | Steiner et al. ......... 424/455 |
| 4,968,590 A |   | 11/1990 | Kuberasampath et al. ... 530/326 |
| 5,011,486 A |   | 4/1991 | Aebischer et al. ...... 606/152 |
| 5,091,513 A |   | 2/1992 | Huston et al. ......... 530/387 |
| 5,225,204 A | * | 7/1993 | Chen et al. ........... 424/484 |
| 5,231,000 A |   | 7/1993 | Majocha et al. ........ 435/7.1 |
| 5,304,121 A | * | 4/1994 | Sahatjian ............. 604/509 |
| 5,410,016 A |   | 4/1995 | Hubbell et al. ........ 528/354 |

(Continued)

FOREIGN PATENT DOCUMENTS

CN 1126589 7/1996

(Continued)

OTHER PUBLICATIONS

Tomanek et al. *Cell. Mol. Biol. Res.*, 40(2):129-136 (1994).

(Continued)

*Primary Examiner*—Gollamudi S Kishore
(74) *Attorney, Agent, or Firm*—Mintz, Levin, Cohn, Ferris, Blovsky and Popeo, P.C.; Ivor R. Elrifi; Christina K. Stock

(57) ABSTRACT

Disclosed are methods of treating subjects having conditions related to angiogenesis including administering an effective amount of a polymeric form of thyroid hormone, or an antagonist thereof, to promote or inhibit angiogenesis in the subject. Compositions of the polymeric forms of thyroid hormone, or thyroid hormone analogs, are also disclosed.

4 Claims, 23 Drawing Sheets

U.S. PATENT DOCUMENTS

| | | | | |
|---|---|---|---|---|
| 5,438,126 | A | * | 8/1995 | DeGroot et al. ............ 536/23.5 |
| 5,591,709 | A | * | 1/1997 | Lindenbaum ................... 514/4 |
| 5,593,688 | A | | 1/1997 | Baldeschwieler ........... 424/450 |
| 5,648,506 | A | * | 7/1997 | Desai et al. .................. 549/510 |
| 5,766,635 | A | * | 6/1998 | Spenleuhauer et al. ...... 424/489 |
| 6,139,870 | A | * | 10/2000 | Verrecchia ................... 424/450 |
| 6,316,412 | B1 | * | 11/2001 | Ginsberg et al. .............. 514/15 |
| 6,482,406 | B1 | | 11/2002 | Stewart .................... 424/93.21 |
| 6,740,680 | B1 | | 5/2004 | Danforth, Jr. et al. ....... 514/570 |
| 2002/0151594 | A1 | | 10/2002 | Morkin et al. .............. 514/567 |
| 2003/0138557 | A1 | * | 7/2003 | Allison ..................... 427/213.3 |
| 2003/0157098 | A1 | * | 8/2003 | Laug ........................ 424/143.1 |
| 2003/0162758 | A1 | * | 8/2003 | Schwartz et al. ............ 514/172 |
| 2003/0165576 | A1 | * | 9/2003 | Fujii et al. .................. 424/649 |
| 2004/0033259 | A1 | * | 2/2004 | Hanshew et al. ............. 424/465 |
| 2005/0249721 | A1 | * | 11/2005 | Houston et al. .......... 424/130.1 |

FOREIGN PATENT DOCUMENTS

| | | |
|---|---|---|
| WO | WO 95/00135 | 1/1995 |
| WO | 96/40048 * | 12/1996 |
| WO | WO 98/33942 | 8/1998 |
| WO | WO 98/56771 | 12/1998 |
| WO | WO 99/62549 | 12/1999 |
| WO | WO 00/78815 A1 | 12/2000 |
| WO | WO 01/13936 A1 | 3/2001 |
| WO | 02/03914 * | 1/2002 |
| WO | WO 02/49501 A2 | 6/2002 |
| WO | WO 02/060389 A2 | 8/2002 |
| WO | WO 03/075741 A2 | 9/2003 |
| WO | WO 2004/013728 A2 | 2/2004 |
| WO | WO 2005/027895 A2 | 3/2005 |
| WO | WO 2006/031922 A2 | 3/2006 |
| WO | WO 2008/051291 A2 | 5/2008 |

OTHER PUBLICATIONS

Tomanek et al. *Circ. Res.*, 82(5):587-593 (1998).
Tomanek et al. *J. Mol. Cell. Cardiol.*, 30(5):923-932 (1998).
Wang et al. *Am. J. Physiol. Heart Circ. Physiol.*, 284(2):H613-H618 (2003).
International Search Report for PCT/US2004/030583, mailing date Mar. 7, 2005.
Database BIOSIS [Online], Accession No. PREV200400161659, Abstract, Mousa et al., "Disclovery of pro-angiogenic effects of thyroid hormone and analogs", *Blood*, 102(11):77b-78b (2003).
Pujol et al., "Letter to the editors: Prevention of thyroid neoplasm recurrence with Triac and levothyroxine", *Clin. Endocrinol.*, 46:121-122 (1997).
Alexis et al., "Nonocclusive Common Carotid Artery Thrombosis in the Rat Results in Reversible Sensorimotor and Cognitive Behavioral Deficits", *Stroke*, 26:2338-2346 (1995).
Ali et al., "Angiogenesis as a potential biomarker in prostate cancer chemoprevention trials", *Urology*, 57(Suppl 4A):143-147 (2001).
Ali et al., "High levels of oestrogen receptor-α in tumorigenesis: inhibition of cell growth and angiogenic factors", *Cell Prolif.*, 34(4):223-231 (2001).
Allen, A.R., "Surgery of experimental lesion of spinal cord equivalent to crush injury of fracture dislocation of spinal column", *J. Am. Med. Assoc.*, 57(11):878-880 (1911).
Amirkhosravi et al., "Antimetastatic effect of tinzaparin, a low-molecular-wight heparin", *J. Thromb. Haemost.*, 1:1972-1976 (2003).
Amirkhosravi et al., "Inhibition of tumor cell-induced platelet aggregation and lung metastasis by the oral GpIIb/IIIa antagonist XV454", *J. Thrombosis and Haemostasis*, 3:549-554 (2003).
Audus et al., "Bovine Brain Microvessel Endothelial Cell Monolayers as a Model System for the Blood-Brain Barrier", in Biological Approaches to the Controlled Delivery of Drugs, *Ann. N.Y. Acad. Sci.*, 507:9-18 (1987).
Avis, K.E., "Parenteral Preparations", in *Remington's Pharmaceutical Sciences, 15th Ed.*, Chapter 84, pp. 1461-1487, Mack Publishing Co., Easton, Pennsylvania (1975).

Bederson et al., "Rat Middle Cerebral Artery Occlusion: Evaluation of the Model and Development of a Neurologic Examination", *Stroke*, 17(3):472-476 (1986).
Benedetti et al., "Life Tables and Survivor Functions", in BMDP Statistical Software Manual, BMDP Statistical Software, Inc., vol. 2, p. 573 and 689-718 (1988).
Bennett et al., "A peptide derived from α-fetoprotein prevents the growth of estrogen-dependent human breast cancers sensitive and resistant to tamoxifen", *Proc. Natl. Acad. Sci. USA*, 99(4):2211-2215 (2002).
Bergstrom et al., "Iodine-123 labelled Z-(R,R)-IQNP: a potential radioligand for visualization of $M_1$ and $M_2$ muscarinic acetylcholine receptors in Alzheimer's disease", *Eur. J. Nucl. Med.*, 26(11):1482-1485 (1999).
Bhat et al., "NCAM-180, the largest component of the neural cell adhesion molecule, is reduced in dysmyelinating quaking mutant mouse brain", *Brain Res.*, 452:373-377 (1988).
Blight, A.R., "Macrophages and Inflammatory Damage in Spinal Cord Injury", *J. Neurotrauma*, 9(Suppl. 1):S83-S91 (1992).
Blood et al., "Tumor interactions with the vasculature: angiogenesis and tumor metastasis", *Bioch. Biophys. Acta*, 1032:89-118 (1990).
Bornebroek et al., "Potential for imaging cerebral amyloid deposits using $^{123}$I-labelled serum amyloid P component and SPET", *Nucl. Med. Commun.*, 17:929-933 (1996).
Bozarth et al., "An improved method for the quantitation of cellular migration: Role of αvβ3 integrin in endothelial and smooth muscle cell migration", *Meth. Cell Sci.*, 19(3):179-187 (1997).
Braughler et al., "Involvment of Lipid Peroxidation in CNS Injury", *J. Neurotrauma*, 9(Suppl. 1):S1-S7 (1992).
Breier et al., "The role of vascular endothelial growth factor in blood vessel formation", *Trends in Cell Biol.*, 6:454-456 (1996).
Carmeliet et al., "Molecular Basis of Angiogenesis Role of VEGF and VE-Cadherin", *Ann. N.Y. Acad. Sci.*, 902:249-264 (2000).
Chanoine et al., "The role of transthyretin in the transport of thyroid hormone to cerebrospinal fluid and brain", *Acta Medica Austriaca*, 19(Suppl. 1):25-28 (1992).
Charness et al., "Ethanol Increases the Expression of Functional Delta-Opioid Receptors in Neuroblastoma x Glioma NG108-15 Hybrid Cells", *J. Biol. Chem.*, 261(7):3164-3169 (1986).
Chavakis et al., "Kinetics of integrin expression in the mouse model of proliferative retinopathy and success of secondary intervention with cyclic RGD peptides", *Diabetologia*, 45:262-267 (2002).
Clifton et al., "Marked Protection by Moderate Hypothermia After Experimental Traumatic Brain Injury", *J. Cereb. Blood Flow Metab.*, 11(1):114-121 (1991).
De la Cruz et al., "Effect of Aspirin Plus Dipyridamole on the Retinal Vascular Pattern in Experimental Diabetes Mellitus", *J. Pharmacol. Exp. Ther.*, 280(1):454-459 (1997).
De Ryck et al., "Neocortical localization of tactile/proprioceptive limb placing reactions in the rat", *Brain Res.*, 573(1):44-60 (1992).
Deardorff, D.L., "Isotonic Solutions", in *Remington's Pharmaceutical Sciences, 15th Ed.*, Chapter 79, pp. 1405-1412, Mack Publishing Co., Easton (1975).
Demediuk et al., "Traumatic Spinal Cord Injury in Rats Causes Increases in Tissue Thromboxane But Not Peptidoleukotrienes", *J. Neurosci. Res.*, 20:115-121 (1988).
Di Chiro et al., "Glucose utilization of cerebral gliomas measured by [$^{18}$F] fluorodeoxyglucose and positron emission tomography", *Neurology*, 32(12):1323-1329 (1982).
Dietrich et al., "Post-traumatic brain hypothermia reduces histopathological damage following concussive brain injury in the rat", *Acta Neuropathol.*, 87(3):250-258 (1994).
Dixon et al., "A fluid percussion model of experimental brain injury in the rat", *J. Neurosurg.*, 67(1):110-119 (1987).
Dupont et al., "Antiangiogenic and antimetastatic properties of Neovastat (Æ-941), an orally active extract derived from cartilage tissue", *Clin. Experim. Metastasis*, 19:145-153 (2002).
Ely and Berne, "Protective Effects of Adenosine in Myocardial Ischemia", *Circulation*, 85:893-904 (1992).
Ethier et al., "Adenosine stimulates proliferation of human endothelial cells in culture", *Am. J. Physiol.*, 265:H131-H138 (1993).

Faden et al., "Endogenous Opioid Immunoreactivity in Rat Spinal Cord Following Traumatic Injury", *Ann. Neurol.*, 17(4):386-390 (1985).

Faden, A.I., "Experimental Neurobiology of Central Nervous System Trauma", *Crit. Rev. Neurobiol.*, 7(3/4):175-186 (1993).

Feeney et al., "Amphetamine, Haloperidol, and Experience Interact to Affect Rate of Recovery After Motor Cortex Injury", *Science*, 217(4562):855-857 (1982).

Feng et al., "Fibrin and Collagen Differentially Regulate Human Dermal Microvascular Endothelial Cell Integrins: Stabilization of $\alpha v/\beta 3$ mRNA by Fibrin", *J. Invest. Dermatol.*, 113(6):913-919 (1999).

Folkman, J., "Angiogenesis in cancer, vascular, rheumatoid and other disease", *Nat. Med.*, 1(1):27-31 (1995).

Freese et al., "Characterization and mechanism of glutamate neurotoxicity in primary striatal cultures", *Brain Res.*, 521(1/2):254-264 (1990).

GenBank Accession No. NM_002210, Jun. 15, 2008.

Goldstein et al., "Influence of Lesion Size and Location on Amphetamine-Facilitated Recovery of Beam-Walking in Rats", *Behav. Neurosci.*, 104(2):320-327 (1990).

Goodman, M.M., "Automated Synthesis of Radiotracers for PET Applications", in *Clinical Positron Emission Tomography*, Mosby Yearbook, K.F. Hubner et al., Chapter 14, pp. 110-122 (1992).

Grant, D.B., "Monitoring TSH concentrations during treatment for congenital hypothyroidism", *Arch. Disease Childhood*, 66:669-670 (1991).

Gregoriadis, "Liposomes", in *Drug Carriers in Biology and Medicine*, Chapter 14, pp. 287-341, Academic Press (1979).

Halks-Miller et al., "CCR1 Immunoreactivity in Alzheimer's Disease Brains", *Society for Neuroscience Meeting*, Abstract #787.6, vol. 24 (1998).

Hansebout, R.R., "A Comprehensive Review of Methods of Improving Cord Recovery After Acute Spinal Cord Injury", in *Early Management of Acute Spinal Cord Injury*, pp. 181-196 (1982).

Hartert, H., "Blutgerinnungsstud Mit Der Thrombelastogeraphie, Einem Neuen Untersuchungsverfahren", *Klinische Wochenschrift*, 26(37/38):577-583 (1948) (in German).

Horuk et al., "Expression of Chemokine Receptors by Subsets of Neurons in the Central Nervous System", *J. Immunol.*, 158:2882-2890 (1997).

Hubner, K.F., "University of Tennessee Biomedical Imaging Center and Transfer of Technology to the Clinical Floor", in *Clinical Positron Emission Tomography*, Mosby Yearbook, K.F. Hubner et al., Chapter 2, pp. 4-16 (1992).

Hudlicka et al., "Factors involved in capillary growth in the heart", *Mol. Cell. Biochem.*, 147:57-68 (1995).

Ingerman-Wojenski et al., "Evaluation of electrical aggregometry: comparison with optical aggregometry, secretion of ATP, and accumulation of radiolabeled platelets", *J. Lab. Clin. Med.*, 101(1):44-52 (1983).

Iwata et al., "A new, convenient method for the preparation of 4-[$^{18}$F]fluorobenzyl halides", *Applied Radiation and Isotopes*, 52(1):87-92 (2000).

Jain, K.K., "Strategies and technologies for drug delivery systems", *TIPS*, 19:155-157 (1998).

Janssen et al., "Pathogenesis of Spinal Cord Injury and Newer Treatments—A Review", *Spine*, 14(1):23-32 (1989).

Kerr et al., "Small molecule $\alpha_v$ integrin antagonists: novel anticancer agents", *Exp. Opin. Invest. Drugs*, 9(6):1271-1279 (2000).

Kim et al., "Regulation of Antiogenesis in Vivo, by Ligation of Integrin $\alpha 5\beta 1$ with the Central Cell-Binding Domain of Fibronectin, *Am. J. Pathol.*, 156(4):1345-1362 (2000).

Kimelberg, H.K., "Astrocytic Edema in CNS Trauma", *J. Neurotrauma*, 9(Suppl. 1):S71-S81 (1992).

Klunk et al., "Development of Small Molecule Probes for the Beta-Amyloid Protein of Alzheimer's Disease", *Neurobiol. Aging*, 15(6):691-698 (1994).

Letterio et al., "Maternal Rescue of Transforming Growth Factor-$\beta 1$ Null Mice", *Science*, 264:1936-1938 (1994).

Liu et al., "Calcineurin Is a Common Target of Cyclophilin-Cyclosporin A and FKBP-FK506 Complexes", *Cell*, 66:807-815 (1991).

Lyons et al., "The Expression of an N-CAM Serum Fragment is Positively Correlated with Severity of Negative Features in Type II Schizophrenia", *Biol. Psychiatry*, 23:769-775 (1988).

Mahmood et al., "An $N_2S_2$ Tetradentate Chelate for Solid-Phase Synthesis: Evaluation in Solution and Solid Phase and Characterization of Technetium-99 Complexes", *Technetium, Rhenium and Other Metals in Chemistry and Nuclear Medicine*, 5:71-76 (1999).

Markgraf et al., "Sensorimotor and cognitive consequences of middle cerebral artery occlusion in rats", *Brain Res.*, 575(2):238-246 (1992).

Mezosi et al., "Nongenomic effect of thyroid hormone on free-radical production in human polymorphonuclear leukocytes", *J. Endocrinol.*, 185:121-129 (2005).

Mohamed et al., "Wound healing properties of cimetidine in vitro", *Drug Intell. Clin. Pharm.*, 20(12):973-975 (1986).

Mousa et al., "Proangiogenesis Action of the Thyroid Hormone Analog 3,5-Diiodothyropropionic Acid (DITPA) Is Initiated at the Cell Surface and Is Integrin Mediated", *Endocrinol.*, 147(4):1602-1607 (2006).

Mousa et al., "Pro-angiogenesis action of thyroid hormone and analogs in a three-dimensional in vitro microvascular endothelial sprouting model", *Int. Angiol.*, 25(4):407-413 (2006).

Mousa et al., "The Proangiogenic Action of Thyroid Hormone Analogue GC-1 Is Initiated at an Integrin", *J. Cardiovasc. Pharmacol.*, 46(3):356-360 (2005).

Mousa, S.A., "Mechanisms of Angiogenesis: Potential Therapeutic Targets", in *Angiogenesis Inhibitors and Stimulators: Potential Therapeutic Implications*, Landes Bioscience, Georgetown, Texas, Chapter I, pp. 1-12 (2000).

Nehls et al., "A microcarrier-based cocultivation system for the investigation of factors and cells involved in angiogenesis in three-dimensional fibrin matrices in vitro", *Histochem. Cell Biol.*, 104(6):459-466 (1995).

Nehls et al., "A Novel, Microcarrier-Based in Vitro Assay for Rapid and Reliable Quantification of Three-Dimensional Cell Migration and Angiogenesis", *Microvasc. Res.*, 50(3):311-322 (1995).

Okada et al., "A Quantitative in vivo Method of Analyzing Human Tumor-induced Angiogenesis in Mice Using Agarose Microencapsulation and Hemoglobin Enzyme-linked Immunosorbent Assay", *Jpn. J. Cancer Res.*, 86(12):1182-1188 (1995).

Pages et al., "Signaling Angiogenesis via p42/p44 MAP Kinase Cascade", *Ann. N.Y. Acad. Sci.*, 902:187-200 (2000).

Panter et al., "Pretreatment with NMDA antagonists limits release of excitatory amino acids following traumatic brain injury", *Neurosci. Lett.*, 136(2):165-168 (1992).

Pardridge, W.M., "Receptor-Mediated Peptide Transport through the Blood-Brain Barrier", *Endocrine Rev.*, 7(3):314-330 (1986).

Penno et al., "Rapid and quantitative in vitro measurement of cellular chemotaxis and invasion", *Meth. Cell Sci.*, 19:189-195 (1997).

Powell, J., "The Serial Analysis of Gene Expression", in *Meth. Mol. Biol.*, Chapter 20, 99:297-319 (2000).

Remsen et al., "Antibodies to the Neural Cell Adhesion Molecule Disrupt Functional Recovery in Injured Nerves", *Exp. Neurol.*, 110:268-273 (1990).

Risau, W., "Mechanisms of angiogenesis", *Nature*, 386:671-674 (1997).

Saito et al., "Vector-mediated delivery of $^{125}$I-labeled $\beta$-amyloid peptide $A\beta^{1-40}$ through the blood-brain barrier and binding to Alzheimer disease amyloid of the $A\beta^{1-40}$/vector complex", *Proc. Natl. Acad. Sci. USA*, 92:10227-10231 (1995).

SAS/STAT Guide for Personal Computers, Version 6 Edition, p. 717 (1987).

Scanlan et al., "3-Iodothyronamine is an endogenous and rapid-acting derivative of thyroid hormone", *Nat. Med.*, 10(6):638-642 (2004).

Scanlan et al., "Selective thyromimetics: Tissue-selective thyroid hormone analogs", *Curr. Opin. Drug Discov. Dev.*, 4(5):614-622 (2001).

Schreiber et al., "Hormone delivery systems to the brain-transthyretin", *Exp. Clin. Endocrinol Diabetes*, 103(2):75-80 (1995).

Skovronsky et al., "In vivo detection of amyloid plaques in a mouse model of Alzheimer's disease", *Proc. Natl. Acad. Sci. USA*, 97(13):7609-7614 (2000).

Tator et al., "Review of the secondary injury theory of acute spinal cord trauma with emphasis on vascular mechanisms", *J. Neurosurg.*, 75(1):15-26 (1991).

Tomanek et al., "Angiogenesis: New Insights and Therapeutic Potential", *Anatomical Record (New Anat.)*, 261:126-135 (2000).

Van Waes et al., "Effects of the novel $\alpha_v$ integrin antagonist SM256 and cis-platinum on growth of murine squamous cell carcinoma PAM LY8", *Int. J. Oncol.*, 16(6):1189-1195 (2000).

Werdelin et al., "Neuropeptides and neural cell adhesion molecule (NCAM) in CSF from patients with ALS", *Acta Neurol. Scand.*, 79(3):177-181 (1989).

Xia et al., "Chemokines/chemokine receptors in the central nervous system and Alzheimer's disease", *J. NeuroVirol.*, 5:32-41 (1999).

Yanase et al., "Role of N-methyl-D-aspartate receptor in acute spinal cord injury", *J. Neurosurg.*, 83:884-888 (1995).

Young, W., "Role of Calcium in Central Nervous System Injuries", *J. Neurotrauma*, 9(Suppl. 1):S9-S25 (1992).

Young, W., "Secondary injury mechanisms in acute spinal cord injury", *J. Emerg. Med.*, 11:13-22 (1993).

Zhen et al., "Synthesis and Amyloid Binding Properties of Rhenium Complexes: Preliminary Progress Toward a Reagent for SPECT Imaging of Alzheimer's Disease Brain", *J. Med. Chem.*, 42:2805-2815 (1999).

Zhuang et al., "$^{99m}$Tc-Labeled MIBG Derivatives: Novel $^{99m}$Tc Complexes as Myocardial Imaging Agents for Sympathetic Neurons", *Bioconjugate Chem.*, 10:159-168 (1999).

Bergh et al., "Integrin $\alpha_v\beta_3$ contains a cell surface receptor site for thyroid hormone that is linked to activation of mitogen-activated protein kinase and induction of angiogenesis", *Endocrinology*, 146(7):2864-2871 (2009).

Chinese Office Action for Application No. 2004800331846, mailed Nov. 30, 2007, cites CN 1126589.

Fife et al., "Effects of tetracyclines on angiogenesis in vitro", Cancer Letters, 153:75-78 (2000).

\* cited by examiner

T$_4$ and T$_3$ stimulate angiogenesis in the chorioallantoic membrane model

| Treatment | Angiogenesis Index |
| --- | --- |
| PBS | 63 ± 10 |
| T$_3$ (1 nM) | 121 ± 18** |
| T$_4$ (0.1 μM) | 155 ± 11** |

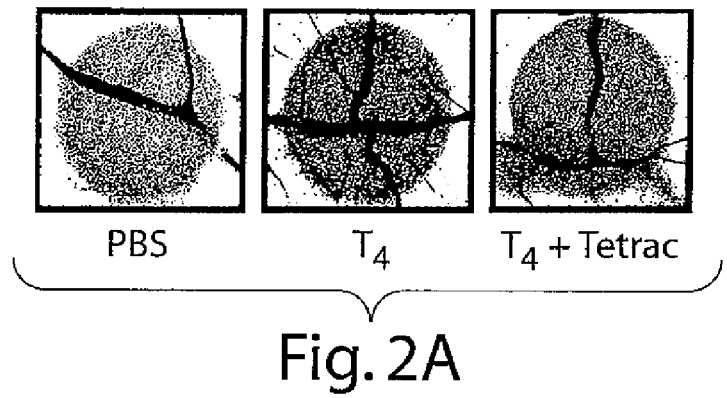
Fig. 2A
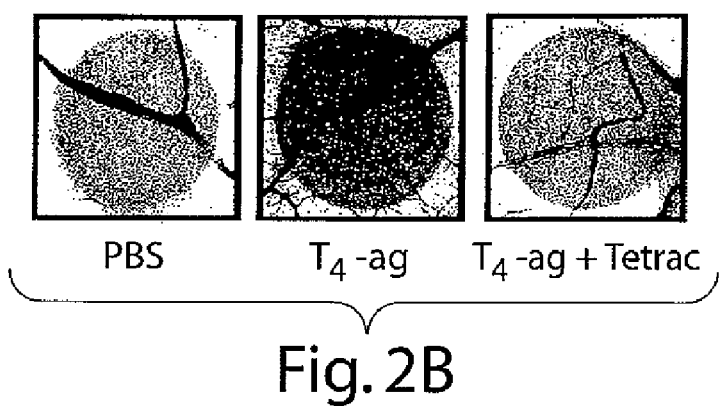
Fig. 2B
Summary of effects of $T_4$ and $T_3$-agarose and tetrac on angiogenesis
| Treatment | Angiogenesis Index |
|---|---|
| PBS | 67 ± 9 |
| $T_4$ (0.1 µM) | 156 ± 16** |
| Tetrac (0.1 µM) | 76 ± 9 |
| $T_4$ + tetrac | 66 ± 6 |
| $T_4$-agarose (0.1 µM) | 194 ± 28** |
| $T_4$-agarose + tetrac | 74 ± 7 |
Fig. 2C Effects of FGF2 and $T_4$ on angiogenesis

| Treatment | Angiogenesis Index |
|---|---|
| PBS | 86 ± 11 |
| FGF2 (0.5 µg/ml) | 126 ± 17* |
| FGF2 (1.0 µg/ml) | 172 ± 9** |
| $T_4$ (0.5 µM) | 115 ± 4* |
| $T_4$ + FGF2 (0.5 µg/ml) | 167 ± 10** |

Effects of FGF2 antibody on angiogenesis stimulated by $T_4$ and FGF2

| Treatment | Angiogenesis Index |
|---|---|
| PBS | 92 ± 10 |
| FGF2 (1.0 μg/ml) | 187 ± 17* |
| FGF2 + FGF2-ab | 118 ± 7 |
| $T_4$ (0.1 μM) | 142 ± 12* |
| $T_4$ + FGF2-ab | 96 ± 10 |

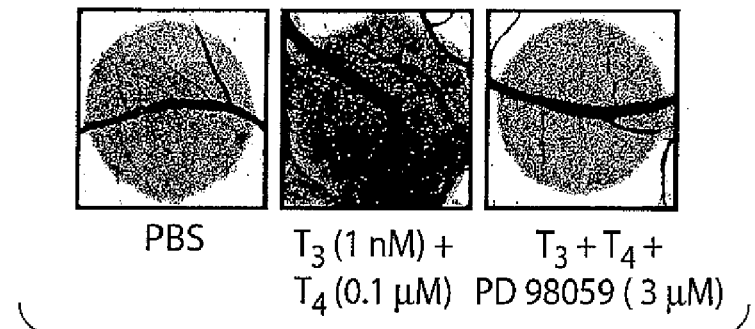
Fig. 5A
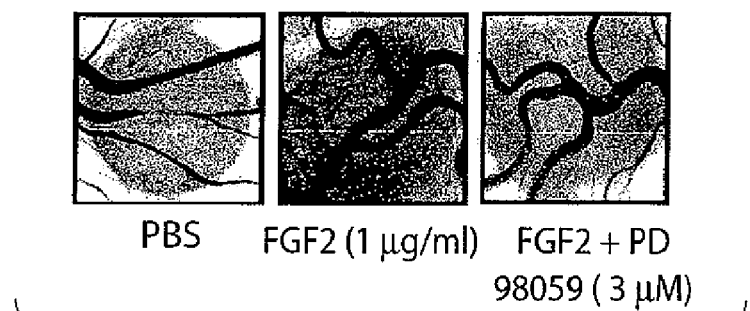
Fig. 5B
Effects of PD 98059 on angiogenesis stimulated by $T_4$ and FGF2
| Treatment | Angiogenesis Index |
| --- | --- |
| PBS | 63 ± 10 |
| $T_3$ (1 nM) + $T_4$ (0.1 μM) | 153 ± 15* |
| $T_3$ + $T_4$ + PD 98059 (3 μM) | 50 ± 10 |
| PBS | 86 ± 11 |
| FGF2 (1 μg/ml) | 191 ± 15** |
| FGF2 + PD 98059 (3 μM) | 110 ± 16 |
Fig. 5C

| CAM treatment | # of Branches ± SEM | % Inhibition ± SEM |
|---|---|---|
| PBS | 73 ± 8 | |
| $T_4$ (0.1 µM) | 170 ± 16 | 0 |
| $T_4$ + LM609 (10 µg) | 109 ± 9 | 64 ± 9 |

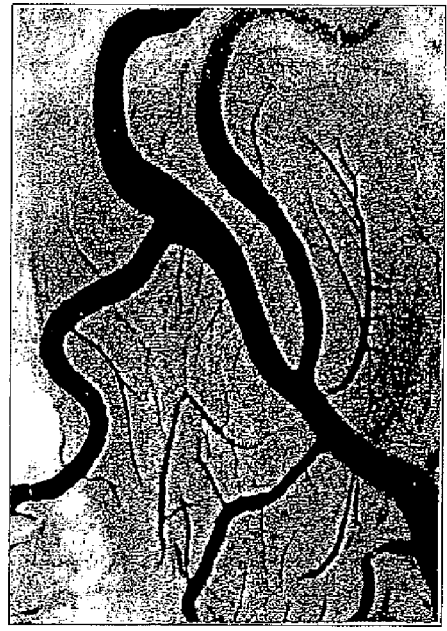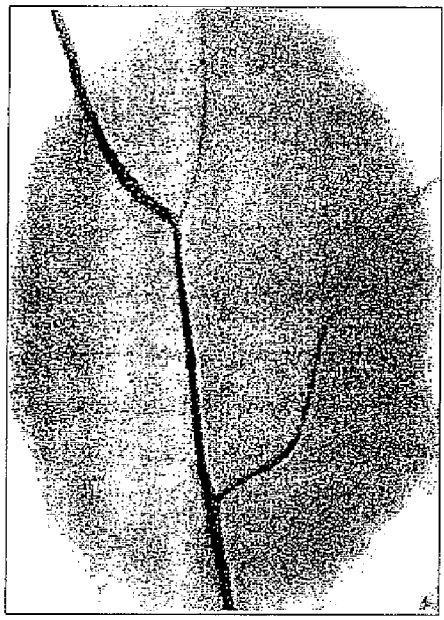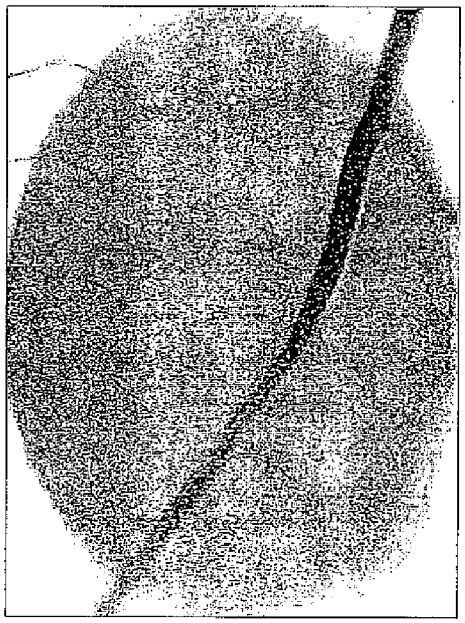
Fig. 16D Inhibitory Effect of αvβ3 integrin antagonists on FGF2-induced angiogenesis in the CAM Model
FGF2 (1 μg) | FGF2 + XT199 | PBS | FGF2 + LM609

Table A

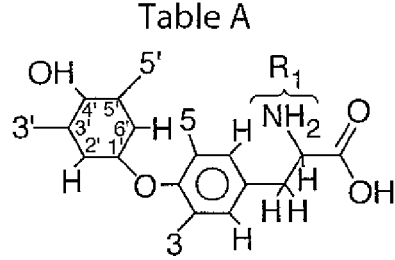

| 3' | 5' | 3 | 5 | $R_1$ | Analogue |
|---|---|---|---|---|---|
| I | I | I | I | $NH_2$ | $L\text{-}T_4$ |
| I | H | I | I | $NH_2$ | $L\text{-}T_3$ |
| I | I | I | H | $NH_2$ | $rT_3$ |
| H | H | I | I | $NH_2$ | $3,5\text{-}L\text{-}T_2$ |
| I | I | H | H | $NH_2$ | $3',5'\text{-}L\text{-}T_2$ |
| I | H | I | H | $NH_2$ | $3,3'\text{-}L\text{-}T_2$ |
| I | H | H | H | $NH_2$ | $3'\text{-}L\text{-}T_3$ |
| Br | Br | Br | Br | $NH_2$ | 3,5,3'-tetrabromo-L-thyronine |
| H | H | Br | Br | $NH_2$ | 3,5,3',-dibromo-L-thyronine |
| Isop[a] | H | Me[b] | Me | $NH_2$ | DIMIT |
| Isop | H | Me | Me | $NH\text{-}COCH_3$ | N-acetyl DIMIT |

[a] Isop, isopropyl
[b] Me, methyl

Fig. 20A

Table B

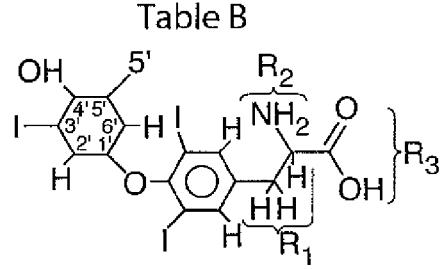

| $R_1$ | $R_2$ | $R_3$ | 5' | Analogue |
|---|---|---|---|---|
| $CH_2CH$ | H | $CO_2H$ | I | 3,5,3',5'-tetraiodothyropropionic acid |
| $CH_2$ | H | $CO_2H$ | I | 3,5,3',5'-tetraiodothyroacetic acid |
| $CH_2$ | H | $CO_2H$ | H | 3,5,3'-triiodothyroacetic acid |
| $CH_2CH$ | $NH_2$ | $COC_2H_5$ | I | $L\text{-}T_4$ ethylester |
| $CH_2CH$ | $NH_2$ | H | H | 3,5,3'-triiodothyronamine |

Fig. 20B

Table C

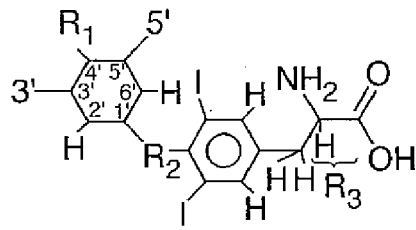

| $R_1$ | $R_2$ | $R_3$ | 3' | 5' | 3 | 5 | Analogue |
|---|---|---|---|---|---|---|---|
| H | O | L | H | H | I | I | 4'-deoxy $T_2$ |
| OH | S | L | I | H | I | I | S-bridged $T_3$ |
| OH | O | D | I | I | I | I | D-$T_4$ |
| OH | O | D | I | H | I | I | D-$T_3$ |

Fig. 20C

Table D

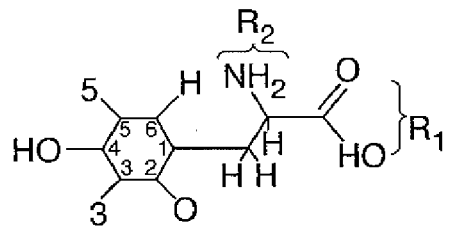

| 3 | 5 | $R_1$ | $R_3$ | Analogue |
|---|---|---|---|---|
| I | I | COOH | $NH_2$ | 3,5-diiodo-L-tyrosine |
| Br | Br | COOH | $NH_2$ | 3,5-dibromo-L-tyrosine |
| Me | Me | COOH | $NH_2$ | 3,5-dimethyl-DL-tyrosine |
| $NO_2$ | $NO_2$ | COOH | $NH_2$ | 3,5-dinitro-L-tyrosine |
| I | H | COOH | $NH_2$ | 3-iodo-L-tyrosine |
| $NO_2$ | H | COOH | $NH_2$ | 3-nitro-L-tyrosine |
| H | H | COOH | $NH_2$ | L-tyrosine |
| I | I | H | $NH_2$ | 3,5-diiodotyramine |
| H | H | H | $NH_2$ | tyramine |
| I | I | COOH | H | 3-(3,5-diiodo-4-hydroxy-phenyl) propionic acid |
| H | H | COOH | H | 3-(p-hydroxy-phenyl) propionic acid |

Fig. 20D

THYROID HORMONE ANALOGS AND METHODS OF USE

RELATED APPLICATIONS

This application claims priority to U.S. Ser. No. 60/502,721, filed Sep. 15, 2003, the content of which is incorporated herein by reference in its entirety.

FIELD OF THE INVENTION

This invention relates to thyroid hormone, thyroid hormone analogs and derivatives, and polymeric forms thereof. Methods of using such compounds, and pharmaceutical compositions containing same are also disclosed. The invention also relates to methods of preparing such compounds.

BACKGROUND OF THE INVENTION

Thyroid hormones, L-thyroxin (T4) and L-triiodothyronine (T3), regulate many different physiological processes in different tissues in vertebrates. Most of the actions of thyroid hormones are mediated by the thyroid hormone receptor ("TR"), which is a member of the nuclear receptor superfamily of ligand-activated transcription regulators. This superfamily also includes receptors for steroid hormones, retinoids, and 1,25-dihydroxyvitamin D3. These receptors are transcription factors that can regulate expression of specific genes in various tissues and are targets for widely used drugs, such as tamoxifen, an estrogen receptor partial antagonist. There are two different genes that encode two different TRs, TRα and TRβ. These two TRs are often co-expressed at different levels in different tissues. Most thyroid hormones do not discriminate between the two TRs and bind both with similar affinities.

Gene knockout studies in mice indicate that TRβ plays a role in the development of the auditory system and in the negative feedback of thyroid stimulating hormone by T3 in the pituitary, whereas TRα modulates the effect of thyroid hormone on calorigenesis and on the cardiovascular system. The identification of TR antagonists could play an important role in the future treatment of hypothyroidism. Such molecules would act rapidly by directly antagonizing the effect of thyroid hormone at the receptor level, a significant improvement for individuals with hypothyroidism who require surgery, have cardiac disease, or are at risk for life-threatening thyrotoxic storm.

Thus, there remains a need for the development of compounds that selectively modulate thyroid hormone action by functioning as isoform-selective agonists or antagonists of the thyroid hormone receptors (TRs) would prove useful for medical therapy. Recent efforts have focused on the design and synthesis of thyroid hormone (T3/T4) antagonists as potential therapeutic agents and chemical probes. There is also a need for the development of thyromimetic compounds that are more accessible than the natural hormone and have potentially useful receptor binding and activation properties.

It is estimated that five million people are afflicted with chronic stable angina in the United States. Each year 200,000 people under the age of 65 die with what is termed "premature ischemic heart disease." Despite medical therapy, many go on to suffer myocardial infarction and debilitating symptoms prompting the need for revascularization with either percutaneous transluminal coronary angioplasty or coronary artery bypass surgery. It has been postulated that one way of relieving myocardial ischemia would be to enhance coronary collateral circulation.

Correlations have now been made between the anatomic appearance of coronary collateral vessels ("collaterals") visualized at the time of intracoronary thrombolitic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized. When the cardiac myocyte is rendered ischemic, collaterals develop actively by growth with DNA replication and mitosis of endothelial and smooth muscle cells. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

During ischemia, adenosine is released through the breakdown of ATP. Adenosine participates in many cardio-protective biological events. Adenosine has a role in hemodynamic changes such as bradycardia and vasodilation, and adenosine has been suggested to have a role in such unrelated phenomena as preconditioning and possibly the reduction in reperfusion injury (Ely and Berne, Circulation, 85: 893 (1992).

Angiogenesis is the development of new blood vessels from preexisting blood vessels (Mousa, S. A., In *Angiogenesis Inhibitors and Stimulators: Potential Therapeutic Implications,* Landes Bioscience, Georgetown, Tex.; Chapter 1, (2000)). Physiologically, angiogenesis ensures proper development of mature organisms, prepares the womb for egg implantation, and plays a key role in wound healing. The development of vascular networks during embryogenesis or normal and pathological angiogenesis depends on growth factors and cellular interactions with the extracellular matrix (Breier et al., *Trends in Cell Biology* 6:454-456 (1996); Folkman, *Nature Medicine* 1:27-31 (1995); Risau, *Nature* 386: 671-674 (1997). Blood vessels arise during embryogenesis by two processes: vasculogenesis and angiogenesis (Blood et al., *Bioch. Biophys. Acta* 1032:89-118 (1990). Angiogenesis is a multi-step process controlled by the balance of pro- and anti-angiogenic factors. The latter stages of this process involve proliferation and the organization of endothelial cells (EC) into tube-like structures. Growth factors such as FGF2 and VEGF are thought to be key players in promoting endothelial cell growth and differentiation.

Control of angiogenesis is a complex process involving local release of vascular growth factors (P Carmeliet, Ann NY Acad Sci 902:249-260, 2000), extracellular matrix, adhesion molecules and metabolic factors (R J Tomanek, G C Schatteman, Anat Rec 261:126-135, 2000). Mechanical forces within blood vessels may also play a role (O Hudlicka, Molec Cell Biochem 147:57-68, 1995). The principal classes of endogenous growth factors implicated in new blood vessel growth are the fibroblast growth factor (FGF) family and vascular endothelial growth factor (VEGF)(G Pages, Ann NY Acad Sci 902:187-200, 2000). The mitogen-activated protein kinase (MAPK; ERK1/2) signal transduction cascade is involved both in VEGF gene expression and in control of proliferation of vascular endothelial cells.

Intrinsic adenosine may facilitate the coronary flow response to increased myocardial oxygen demands and so modulate the coronary flow reserve (Ethier et al., Am. J. Physiol., H131 (1993) demonstrated that the addition of physiological concentrations of adenosine to human umbilical vein endothelial cell cultures stimulates proliferation, possibly via a surface receptor. Adenosine may be a factor for human endothelial cell growth and possibly angiogenesis. Angiogenesis appears to be protective for patients with obstructive blood flow such as coronary artery disease ("CAD"), but the rate at which blood vessels grow naturally is inadequate to reverse the disease. Thus, strategies to enhance and accelerate the body's natural angiogenesis potential should be beneficial in patients with CAD.

Similarly, wound healing is a major problem in many developing countries and diabetics have impaired wound healing and chronic inflammatory disorders, with increased use of various cyclooxygenase-2 (CoX2) inhibitors. Angiogenesis is necessary for wound repair since the new vessels provide nutrients to support the active cells, promote granulation tissue formation and facilitate the clearance of debris. Approximately 60% of the granulation tissue mass is composed of blood vessels which also supply the necessary oxygen to stimulate repair and vessel growth. It is well documented that angiogenic factors are present in wound fluid and promote repair while antiangiogenic factors inhibit repair. Wound angiogenesis is a complex multi-step process. Despite a detailed knowledge about many angiogenic factors, little progress has been made in defining the source of these factors, the regulatory events involved in wound angiogenesis and in the clinical use of angiogenic stimulants to promote repair. Further complicating the understanding of wound angiogenesis and repair is the fact that the mechanisms and mediators involved in repair likely vary depending on the depth of the wound, type of wound (burn, trauma, etc.), and the location (muscle, skin, bone, etc.). The condition and age of the patient (diabetic, paraplegic, on steroid therapy, elderly vs infant, etc) can also determine the rate of repair and response to angiogenic factors. The sex of the patient and hormonal status (premenopausal, post menopausal, etc.) may also influence the repair mechanisms and responses. Impaired wound healing particularly affects the elderly and many of the 14 million diabetics in the United States. Because reduced angiogenesis is often a causative agent for wound healing problems in these patient populations, it is important to define the angiogenic factors important in wound repair and to develop clinical uses to prevent and/or correct impaired wound healing.

Thus, there remains a need for an effective therapy in the way of angiogenic agents as either primary or adjunctive therapy for promotion of wound healing, coronary angiogenesis, or other angiogenic-related disorders, with minimum side effects. Such a therapy would be particularly useful for patients who have vascular disorders such as myocardial infarctions, stroke or peripheral artery diseases and could be used prophylactically in patients who have poor coronary circulation, which places them at high risk of ischemia and myocardial infarctions.

It is interesting to note that angiogenesis also occurs in other situations, but which are undesirable, including solid tumour growth and metastasis; rheumatoid arthritis; psoriasis; scleroderma; and three common causes of blindness—diabetic retinopathy, retrolental fibroplasia and neovascular glaucoma (in fact, diseases of the eye are almost always accompanied by vascularization. The process of wound angiogenesis actually has many features in common with tumour angiogenesis. Thus, there are some conditions, such as diabetic retinopathy or the occurrence of primary or metastatic tumors, where angiogenesis is undesirable. Thus, there remains a need for methods by which to inhibit the effect of angiogenic agents.

SUMMARY OF THE INVENTION

The invention is based, in part, on the discovery that thyroid hormone, thyroid hormone analogs, and their polymeric forms, act at the cell membrane level and have pro-angiogenic properties that are independent of the nuclear thyroid hormone effects. Accordingly, these thyroid hormone analogs and polymeric forms (i.e., angiogenic agents) can be used to treat a variety of disorders. Similarly, the invention is also based on the discovery that thyroid hormone analog antagonists inhibit the pro-angiogenic effect of such analogs, and can also be used to treat a variety of disorders.

Accordingly, in one aspect the invention features methods for treating a condition amenable to treatment by promoting angiogenesis by administering to a subject in need thereof an amount of a polymeric form of thyroid hormone, or an analog thereof, effective for promoting angiogenesis. Examples of such conditions amenable to treatment by promoting angiogenesis are provided herein and can include occlusive vascular disease, coronary disease, erectile dysfunction, myocardial infarction, ischemia, stroke, peripheral artery vascular disorders, and wounds.

Examples of thyroid hormone analogs are also provided herein and can include triiodothyronine (T3), levothyroxine (T4), 3,5-dimethyl-4-(4'-hydroy-3'-isopropylbenzyl)-phenoxy acetic acid (GC-1), or 3,5-diiodothyropropionic acid (DITPA), tetraiodothyroacetic acid (TETRAC), and triiodothyroacetic acid (TRIAC). Additional analogs are in FIG. 20 Tables A-D. These analogs can be conjugated to polyvinyl alcohol, acrylic acid ethylene co-polymer, polylactic acid, or agarose. The conjugation is via covalent or non-covalent bonds depending on the polymer used.

In one embodiment the thyroid hormone, thyroid hormone analogs, or polymeric forms thereof are administered by parenteral, oral, rectal, or topical means, or combinations thereof. Parenteral modes of administration include, for example, subcutaneous, intraperitoneal, intramuscular, or intravenous modes, such as by catheter. Topical modes of administration can include, for example, a band-aid.

In another embodiment, the thyroid hormone, thyroid hormone analogs, or polymeric forms thereof can be encapsulated or incorporated in a microparticle, liposome, or polymer. The polymer can include, for example, polyglycolide, polylactide, or co-polymers thereof. The liposome or microparticle has a size of about less than 200 nanometers, and can be administered via one or more parenteral routes, or another mode of administration. In another embodiment the liposome or microparticle can be lodged in capillary beds surrounding ischemic tissue, or applied to the inside of a blood vessel via a catheter.

Thyroid hormone, thyroid hormone analogs, or polymeric forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or combinations thereof. In one embodiment, the thyroid hormone analog or polymeric form is administered as a bolus injection prior to or post-administering one or more biologically active substance.

Growth factors can include, for example, transforming growth factor alpha (TGFα), transforming growth factor beta (TGFβ), basic fibroblast growth factor, vascular endothelial growth factor, epithelial growth factor, nerve growth factor, platelet-derived growth factor, and vascular permeability factor. Vasodilators can include, for example, adenosine, adenosine derivatives, or combinations thereof. Anticoagulants include, but are not limited to, heparin, heparin derivatives, anti-factor Xa, anti-thrombin, aspirin, clopidgrel, or combinations thereof.

In another aspect of the invention, methods are provided for promoting angiogenesis along or around a medical device by coating the device with a thyroid hormone, thyroid hormone analog, or polymeric form thereof according to the invention prior to inserting the device into a patient. The coating step can further include coating the device with one or more biologically active substance, such as, but not limited to, a growth factor, a vasodilator, an anti-coagulant, or combinations thereof. Examples of medical devices that can be coated with thyroid hormone analogs or polymeric forms according to the invention include stents, catheters, cannulas or electrodes.

In a further aspect, the invention provides methods for treating a condition amenable to treatment by inhibiting angiogenesis by administering to a subject in need thereof an amount of an anti-angiogenesis agent effective for inhibiting angiogenesis.

Examples of the conditions amenable to treatment by inhibiting angiogenesis include, but are not limited to, primary or metastatic tumors, diabetic retinopathy, and related conditions. Examples of the anti-angiogenesis agents used for inhibiting angiogenesis are also provided by the invention and include, but are not limited to, tetraiodothyroacetic acid (TETRAC), triiodothyroacetic acid (TRIAC), monoclonal antibody LM609, XT 199 or combinations thereof. Such anti-angiogenesis agents can act at the cell surface to inhibit the pro-angiogenesis agents.

In one embodiment, the anti-angiogenesis agent is administered by a parenteral, oral, rectal, or topical mode, or combination thereof. In another embodiment, the anti-angiogenesis agent can be co-administered with one or more anti-angiogenesis therapies or chemotherapeutic agents.

In yet a further aspect, the invention provides compositions (i.e., angiogenic agents) that include thyroid hormone, and analogs conjugated to a polymer. The conjugation can be through a covalent or non-covalent bond, depending on the polymer. A covalent bond can occur through an ester or anhydride linkage, for example. Examples of the thyroid hormone analogs are also provided by the instant invention and include levothyroxine (T4), triiodothyronine (T3), 3,5-dimethyl-4-(4'-hydroy-3'-isopropylbenzyl)-phenoxy acetic acid (GC-1), or 3,5-diiodothyropropionic acid (DITPA). In one embodiment, the polymer can include, but is not limited to, polyvinyl alcohol, acrylic acid ethylene co-polymer, polylactic acid, or agarose.

In another aspect, the invention provides for pharmaceutical formulations including the angiogenic agents according to the present invention in a pharmaceutically acceptable carrier. In one embodiment, the pharmaceutical formulations can also include one or more pharmaceutically acceptable excipients.

The pharmaceutical formulations according to the present invention can be encapsulated or incorporated in a liposome, microparticle, or polymer. The liposome or microparticle has a size of less than about 200 nanometers. Any of the pharmaceutical formulations according to the present invention can be administered via parenteral, oral, rectal, or topical means, or combinations thereof. In another embodiment, the pharmaceutical formulations can be co-administered to a subject in need thereof with one or more biologically active substances including, but not limited to, growth factors, vasodilators, anti-coagulants, or combinations thereof.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference in their entirety.

BRIEF DESCRIPTION OF THE DRAWINGS

FIG. 2. Tetrac inhibits stimulation of angiogenesis by T4 and agarose-linked T4 (T4-ag). A, A 2.5-fold increase in blood vessel branch formation is seen in a representative CAM preparation exposed to 0.1 µmol/L T4 for 3 days. In 3 similar experiments, there was a 2.3-fold increase. This effect of the hormone is inhibited by tetrac (0.1 µmol/L), a T4 analogue shown previously to inhibit plasma membrane actions of T4.13 Tetrac alone does not stimulate angiogenesis (C). B, T4-ag (0.1 µmol/L) stimulates angiogenesis 2.3-fold (2.9-fold in 3 experiments), an effect also blocked by tetrac. C, Summary of the results of 3 experiments that examine the actions of tetrac, T4-ag, and T4 in the CAM assay. Data (means±SEM) were obtained from 10 images for each experimental condition in each of 3 experiments. **$P<0.001$ by ANOVA, comparing T4-treated and T4-agarose-treated samples with PBS-treated control samples.

FIG. 5. Effect of PD 98059, a MAPK (ERK1/2) signal transduction cascade inhibitor, on angiogenesis induced by T4, T3, and FGF2. A, Angiogenesis stimulated by T4 (0.1 μmol/L) and T3 (1 nmol/L) together is fully inhibited by PD 98059 (3 μmol/L). B, Angiogenesis induced by FGF2 (1 μg/mL) is also inhibited by PD 98059, indicating that the action of the growth factor is also dependent on activation of the ERK1/2 pathway. In the context of the experiments involving T4-agarose (T4-ag) and tetrac (FIG. 2) indicating that T4 initiates its proangiogenic effect at the cell membrane, results shown in A and B are consistent with 2 roles played by MAPK in the proangiogenic action of thyroid hormone: ERK1/2 transduces the early signal of the hormone that leads to FGF2 elaboration and transduces the subsequent action of FGF2 on angiogenesis. C, Summary of results of 3 experiments, represented by A and B, showing the effect of PD98059 on the actions of T4 and FGF2 in the CAM model. *P<0.01; **P<0.001, indicating results of ANOVA on data from 3 experiments.

FIG. 20. Thyroid Hormone Analogs Capable of Conjugation with Various Polymers. A-D show substitutions required to achieve various thyroid hormone analogs which can be conjugated to create polymeric forms of thyroid hormone analogs of the invention.

DETAILED DESCRIPTION OF THE INVENTION

Figures 1A, 1B:
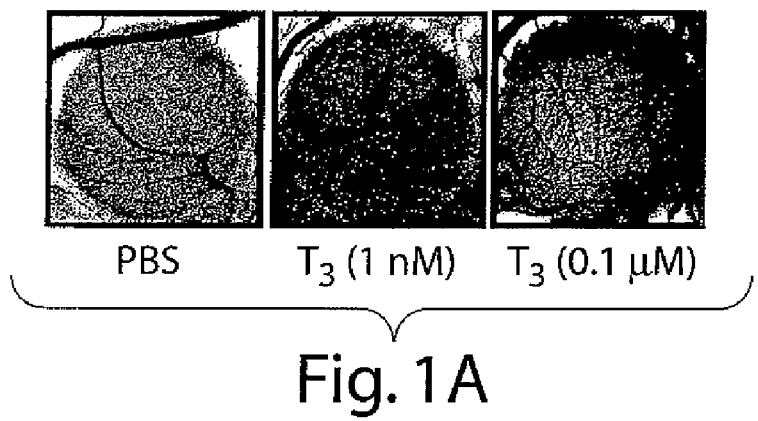
FIG. 1. Effects of L-T4 and L-T3 on angiogenesis quantitated in the chick CAM assay. A, Control samples were exposed to PBS and additional samples to 1 nM T3 or 0.1 µmol/L T4 for 3 days. Both hormones caused increased blood vessel branching in these representative images from 3 experiments. B, Tabulation of mean±SEM of new branches formed from existing blood vessels during the experimental period drawn from 3 experiments, each of which included 9 CAM assays. At the concentrations shown, T3 and T4 caused similar effects (1.9-fold and 2.5-fold increases, respectively, in branch formation). **$P<0.001$ by 1-way ANOVA, comparing hormone-treated with PBS-treated CAM samples.

The features and other details of the invention will now be more particularly described with references to the accompanying drawings, and as pointed out by the claims. For convenience, certain terms used in the specification, examples and claims are collected here. Unless otherwise defined, all technical and scientific terms used herein have the same meaning as commonly understood by one of ordinary skill in the art to which this invention pertains.

As used herein, the term "angiogenic agent" includes any compound or substance that promotes or encourages angiogenesis, whether alone or in combination with another substance. Examples include, but are not limited to, T3, T4, T3 or T4-agarose, polymeric analogs of T3, T4, 3,5-dimethyl-4-(4'-hydroy-3'-isopropylbenzyl)-phenoxy acetic acid (GC-1), or DITPA. In contrast, the terms "anti-angiogenesis agent" or anti-angiogenic agent" refer to any compound or substance that inhibits or discourages angiogenesis, whether alone or in combination with another substance. Examples include, but are not limited to, TETRAC, TRIAC, XT 199, and mAb LM609.

As used herein, the term "myocardial ischemia" is defined as an insufficient blood supply to the heart muscle caused by a decreased capacity of the heart vessels. As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related the term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

"Pharmaceutically acceptable salts" refers to pharmaceutically acceptable salts of thyroid hormone analogs, polymeric forms, and derivatives, which salts are derived from a variety of organic and inorganic counter ions well known in the art and include, by way of example only, sodium, potassium, calcium, magnesium, ammonium, tetra-alkyl ammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

"Subject" includes living organisms such as humans, monkeys, cows, sheep, horses, pigs, cattle, goats, dogs, cats, mice, rats, cultured cells therefrom, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting angiogenesis. A variety of routes of administration are possible including, but not necessarily limited to parenteral (e.g., intravenous, intra-arterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, *Remington's Pharmaceutical Science,* 16th Edition, Mack, Ed. (1980)).

"Effective amount" includes those amounts of pro-angiogenic or anti-angiogenic compounds which allow it to perform its intended function, e.g., promoting or inhibiting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences.*

Compositions

Disclosed herein are angiogenic agents comprising thyroid hormones, analogs thereof, and polymer conjugations of the hormones and their analogs. The disclosed compositions can be used for promoting angiogenesis to treat disorders wherein angiogenesis is beneficial. Additionally, the inhibition of these thyroid hormones, analogs and polymer conjugations can be used to inhibit angiogenesis to treat disorders associated with such undesired angiogenesis. As used herein, the term "angiogenic agent" includes any compound or substance that promotes or encourages angiogenesis, whether alone or in combination with another substance. Examples include, but are not limited to, T3, T4, T3 or T4-agarose, polymeric analogs of T3, T4, 3,5-dimethyl-4-(4'-hydroy-3'-isopropylbenzyl)-phenoxy acetic acid (GC-1), or DITPA.

Polymer conjugations are used to improve drug viability. While many old and new therapeutics are well-tolerated, many compounds need advanced drug discovery technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain.

Figure 17:
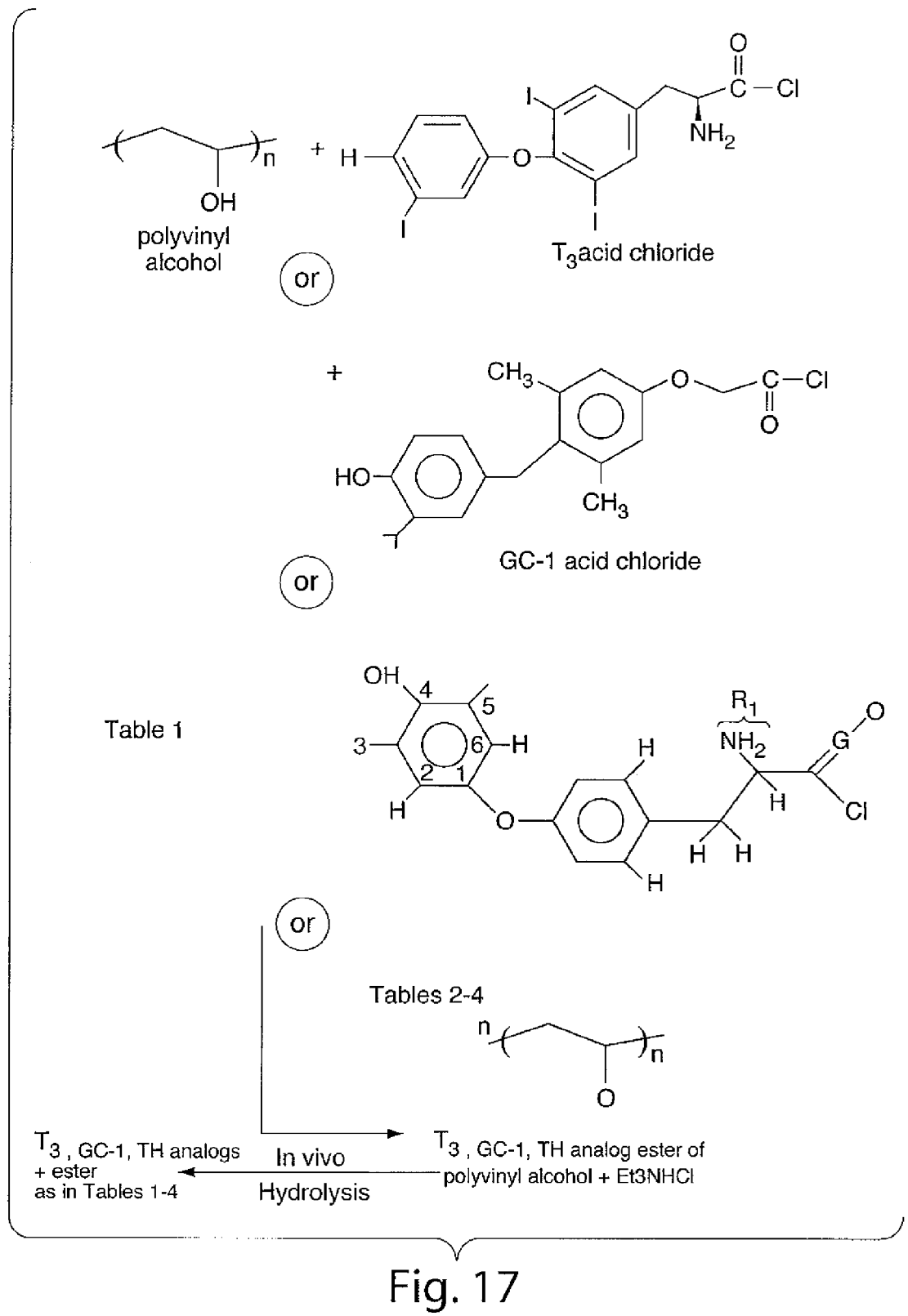
FIG. 17. Polymer Compositions of Thyroid Hormone Analogs—Polymer Conjugation Through an Ester Linkage Using Polyvinyl Alcohol. In this preparation commercially available polyvinyl alcohol (or related co-polymers) can be esterified by treatment with the acid chloride of thyroid hormone analogs, namely the acid chloride form. The hydrochloride salt is neutralized by the addition of triethylamine to afford triethylamine hydrochloride which can be washed away with water upon precipitation of the thyroid hormone ester polymer form for different analogs. The ester linkage to the polymer may undergo hydrolysis in vivo to release the active pro-angiogenesis thyroid hormone analog.

Representative compositions of the present invention include thyroid hormone or analogs thereof conjugated to polymers. Conjugation with polymers can be either through covalent or non-covalent linkages. In preferred embodiments, the polymer conjugation can occur through an ester linkage or an anhydride linkage. An example of a polymer conjugation through an ester linkage using polyvinyl alcohol is shown in FIG. 17. In this preparation commercially available polyvinyl alcohol (or related co-polymers) can be esterified by treatment with the acid chloride of thyroid hormone analogs, including the acid chloride form. The hydrochloride salt is neutralized by the addition of triethylamine to afford triethylamine hydrochloride which can be washed away with water upon precipitation of the thyroid hormone ester polymer form for different analogs. The ester linkage to the polymer may undergo hydrolysis in vivo to release the active pro-angiogenesis thyroid hormone analog.

Figure 18:
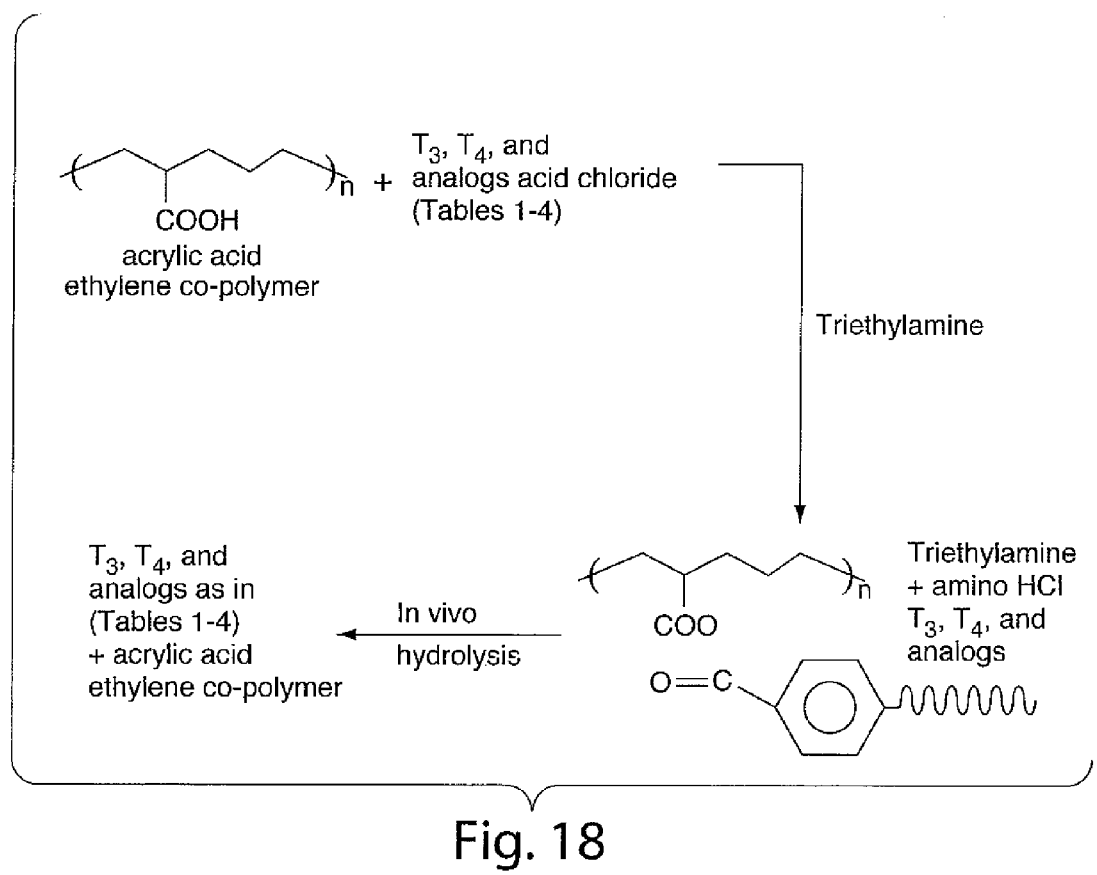
FIG. 18. Polymer Compositions of Thyroid Hormone Analogs—Polymer Conjugation Through an Anhydride Linkage Using Acrylic Acid Ethylene Co-polymer. This is similar to the previous polymer covalent conjugation however this time it is through an anhydride linkage that is derived from reaction of an acrylic acid co-polymer. This anhydride linkage is also susceptible to hydrolysis in vivo to release thyroid hormone analog. Neutralization of the hydrochloric acid is accomplished by treatment with triethylamine and subsequent washing of the precipitated polyanhydride polymer with water removes the triethylamine hydrochloride byproduct. This reaction will lead to the formation of Thyroid hormone analog acrylic acid co-polymer+triethylamine. Upon in vivo hydrolysis, the thyroid hormone analog will be released over time that can be controlled plus acrylic acid ethylene Co-polymer.

An example of a polymer conjugation through an anhydride linkage using acrylic acid ethylene co-polymer is shown in FIG. 18. This is similar to the previous polymer covalent conjugation, however, this time it is through an anhydride linkage that is derived from reaction of an acrylic acid co-polymer. This anhydride linkage is also susceptible to hydrolysis in vivo to release thyroid hormone analog. Neutralization of the hydrochloric acid is accomplished by treatment with triethylamine and subsequent washing of the precipitated polyanhydride polymer with water removes the triethylamine hydrochloride byproduct. This reaction will lead to the formation of Thyroid hormone analog acrylic acid co-polymer+triethylamine. Upon in vivo hydrolysis, the thyroid hormone analog will be released over time that can be controlled plus acrylic acid ethylene Co-polymer.

Another representative polymer conjugation includes thyroid hormone or its analogs conjugated to polyethylene glycol (PEG). Attachment of PEG to various drugs, proteins and liposomes has been shown to improve residence time and decrease toxicity. PEG can be coupled to active agents through the hydroxyl groups at the ends of the chains and via other chemical methods. Peg itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

Figure 19:
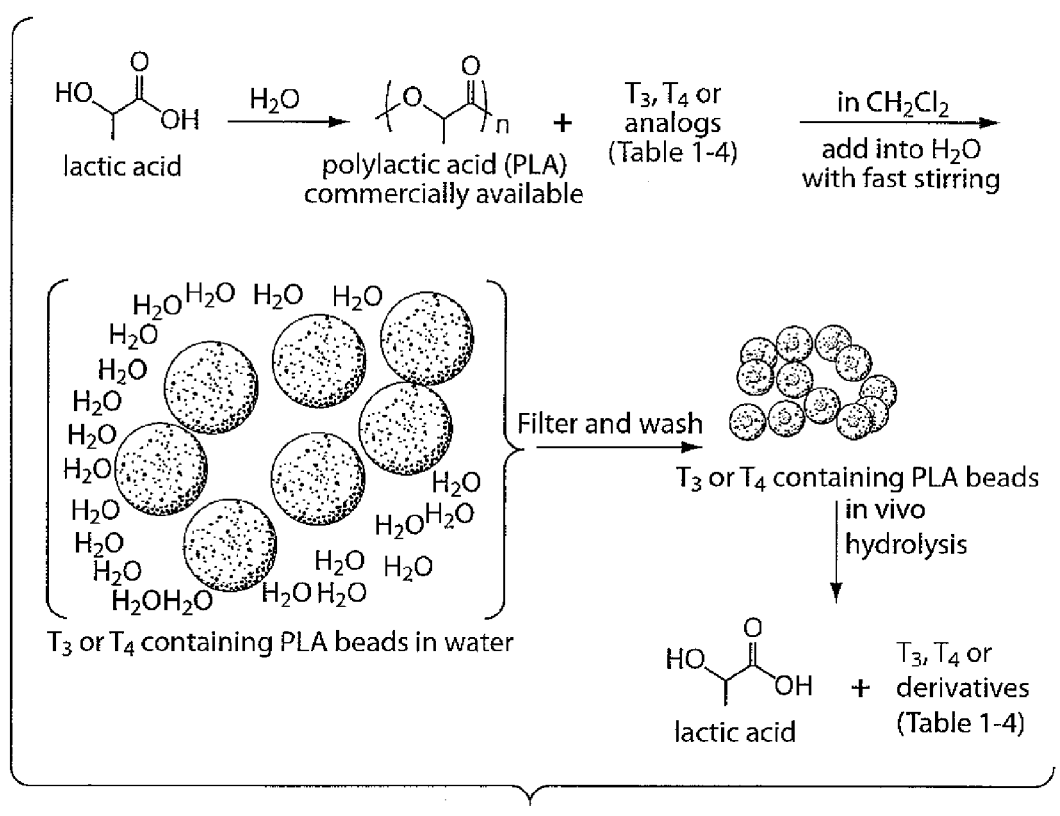
FIG. 19. Polymer Compositions of Thyroid Hormone Analogs—Entrapment in a Polylactic Acid Polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of Thyroid hormone analog containing PLA beads in water. Filter and washing will result in the formation of thyroid hormone analog containing PLA beads, which upon in vivo hydrolysis will lead to the generation of controlled levels of thyroid hormone plus lactic acid.

Another representative polymer conjugation includes thyroid hormone or its analogs in non-covalent conjugation with polymers. This is shown in detail in FIG. 19. A preferred non-covalent conjugation is entrapment of thyroid hormone or analogs thereof in a polylactic acid polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of Thyroid hormone analog containing PLA beads in water. Filter and washing will result in the formation of thyroid hormone analog containing PLA beads, which upon in vivo hydrolysis hydrolysis will lead to the generation of controlled levels of thyroid hormone plus lactic acid.

Furthermore, nanotechnology can be used for the creation of useful materials and structures sized at the nanometer scale. The main drawback with biologically active substances is fragility. Nanoscale materials can be combined with such biologically active substances to dramatically improve the durability of the substance, create localized high concentrations of the substance and reduce costs by minimizing losses. Therefore, additional polymeric conjugations include nanoparticle formulations of thyroid hormones and analogs thereof. In such an embodiment, nano-polymers and nano-particles can be used as a marix for local delivery of thyrid hormone and its analogs. This will aid in time controlled delivery into the cellular and tissue target.

Compositions of the present invention include both thyroid hormone, analogs, and derivatives either alone or in covalent or non-covalent conjugation with polymers. Examples of representative analogs and derivatives are shown in FIG. 20, Tables A-D. Table A shows T2, T3, T4, and bromo-derivatives. Table B shows alanyl side chain modifications. Table C shows hydroxy groups, diphenyl ester linkages, and D-configurations. Table D shows tyrosine analogs.

The terms "anti-angiogenesis agent" or anti-angiogenic agent" refer to any compound or substance that inhibits or discourages angiogenesis, whether alone or in combination with another substance. Examples include, but are not limited to, TETRAC, TRIAC, XT 199, and mAb LM609.

The Role of Thyroid Hormone, Analogs, and Polymeric Conjugations in Promoting Angiogenesis The pro-angiogenic effect of thyroid hormone analogs or polymeric forms depends upon a non-genomic initiation, as tested by the susceptibility of the hormonal effect to reduction by pharmacological inhibitors of the MAPK signal transduction pathway. Such results indicates that another consequence of activation of MAPK by thyroid hormone is new blood vessel growth. The latter is initiated nongenomically, but of course, requires a consequent complex gene transcription program. The ambient concentrations of thyroid hormone are relatively stable. The CAM model, at the time we tested it, was thyroprival and thus may be regarded as a system, which does not reproduce the intact organism.

The availability of a chick chorioallantoic membrane (CAM) assay for angiogenesis has provided a model in which to quantitate angiogenesis and to study possible mechanisms involved in the induction by thyroid hormone of new blood vessel growth. The present application discloses a pro-angiogenic effect of $T_4$ that approximates that in the CAM model of FGF2 and that can enhance the action of suboptimal doses of FGF2. It is further disclosed that the pro-angiogenic effect of the hormone is initiated at the plasma membrane and is dependent upon activation by $T_4$ of the MAPK signal transduction pathway. As provided above, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Thyroid hormone analogs, polymeric forms, and derivatives. The methods involve the co-administration of an effective amount of thyroid hormone analogs, polymeric forms, and derivatives in low, daily dosages for a week or more with other standard pro-angiogenesis growth factors, vasodilators, anticoagulants, thrombolytics or other vascular-related therapies.

The CAM assay has been used to validate angiogenic activity of a variety of growth factors and compounds believed to promote angiogenesis. For example, $T_4$ in physiological concentrations was shown to be pro-angiogenic in this in vitro model and on a molar basis to have the activity of FGF2. The presence of PTU did not reduce the effect of $T_4$, indicating that de-iodination of $T_4$ to generate $T_3$ was not a prerequisite in this model. A summary of the pro-angiogenesis effects of various thyroid hormone analogs is listed in Tabel 1.

TABLE 1

Pro-angiogenesis Effects of Various Thyroid Hormone Analogs in the CAM Model

| TREATMENT | ANGIOGENESIS INDEX |
|---|---|
| PBS (Control) | 89.4 ± 9.3 |
| DITPA (0.01 uM) | 133.0 ± 11.6 |
| DITPA (0.1 uM) | 167.3 ± 12.7 |
| DITPA (0.2 mM) | 117.9 ± 5.6 |

TABLE 1-continued

Pro-angiogenesis Effects of Various Thyroid Hormone
Analogs in the CAM Model

| TREATMENT | ANGIOGENESIS INDEX |
|---|---|
| GC-1 (0.01 uM) | 169.6 ± 11.6 |
| GC-1 (0.1 uM) | 152.7 ± 9.0 |
| T4 agarose (0.1 uM) | 195.5 + 8.5 |
| T4 (0.1 uM) | 143.8 ± 7.9 |
| FGF2 (1 ug) | 155 ± 9 | n = 8 per group

The appearance of new blood vessel growth in this model requires several days, indicating that the effect of thyroid hormone was wholly dependent upon the interaction of the nuclear receptor for thyroid hormone (TR) with the hormone. Actions of iodothyronines that require intranuclear complexing of TR with its natural ligand, $T_3$, are by definition, genomic, and culminate in gene expression. On the other hand, the preferential response of this model system to $T_4$-rather than $T_3$, the natural ligand of TR-raised the possibility that angiogenesis might be initiated nongenomically at the plasma membrane by $T_4$ and culminate in effects that require gene transcription. Non-genomic actions of $T_4$ have been widely described, are usually initiated at the plasma membrane and may be mediated by signal transduction pathways. They do not require intranuclear ligand of iodothyronine and TR, but may interface with or modulate gene transcription. Non-genomic actions of steroids have also been well described and are known to interface with genomic actions of steroids or of other compounds. Experiments carried out with $T_4$ and tetrac or with agarose-$T_4$ indicated that the pro-angiogenic effect of $T_4$ indeed very likely was initiated at the plasma membrane. Tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used to examine models for possible cell surface-initiated actions of the hormone.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, and wounds. Also disclosed are compositions and methods for promoting angiogenesis and/or recruiting collateral blood vessels in a patient in need thereof. The compositions include an effective amount of polymeric forms of thyroid hormone analogs and derivatives and an effective amount of an adenosine and/or nitric oxide donor. The compositions can be in the form of a sterile, injectable, pharmaceutical formulation that includes an angiogenically effective amount of thyroid hormone-like substance and adenosine derivatives in a physiologically and pharmaceutically acceptable carrier, optionally with one or more excipients.

Myocardial Infarction

A major reason for heart failure following acute myocardial infarction is an inadequate response of new blood vessel formation, i.e., angiogenesis. Thyroid hormone and its analogs are beneficial in heart failure and stimulate coronary angiogenesis. The methods of the invention include, in part, delivering a single treatment of a thyroid hormone analog at the time of infarction either by direct injection into the myocardium, or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of thyroid hormone, or an analog thereof, effective for promoting angiogenesis.

Examples of polymeric forms of thyroid hormone analogs are also provided herein and can include triiodothyronine (T3), levothyroxine (T4), (GC-1), or 3,5-diiodothyropropionic acid (DITPA) conjugated to polyvinyl alcohol, acrylic acid ethylene co-polymer, polylactic acid, or agarose.

The methods also involve the co-administration of an effective amount of thyroid hormone-like substance and an effective amount of an adenosine and/or NO donor in low, daily dosages for a week or more. One or both components can be delivered locally via catheter. Thyroid hormone analogs, and derivatives in vivo can be delivered to capillary beds surrounding ischemic tissue by incorporation of the compounds in an appropriately sized liposome or microparticle. Thyroid hormone analogs, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound Healing

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. Growth factors such as keratinocyte growth factor (KGF) mediate this process. Several models (sliding versus rolling cells) of epithelialization exist.

As thyroid hormones regulate metabolic rate, when the metabolism slows down due to hypothyroidism, wound healing also slows down. The role of topically applied thyroid hormone analogs or polymeric forms in wound healing therefore represents a novel strategy to accelerate wound healing in diabetics and in non-diabetics with impaired wound healing abilities. Topical adminstration can be in the form of attachment to a band-aid. Additonally, nano-polymers and nano-particles can be used as a marix for local delivery of thyrid hormone and its analogs. This will aid in time controlled delivery into the cellular and tissue target.

Accordingly, another embodiment of the invention features methods for treating wounds by promoting angiogenesis by administering to a subject in need thereof an amount of a polymeric form of thyroid hormone, or an analog thereof, effective for promoting angiogenesis. For details, see Example 9.

The Role of Thyroid Hormone, Analogs, and Polymeric Conjugations in Inhibiting Angiogenesis The invention also provides, in another part, compositions and methods for inhibiting angiogenesis in a subject in need thereof. Conditions amenable to treatment by inhibiting angiogenesis include, for example, primary or metastatic tumors and diabetic retinopathy. The compositions can include an effective amount of TETRAC, TRIAC or mAb LM609. The compositions can be in the form of a sterile, injectable, pharmaceutical formulation that includes an anti-angiogenically effective amount of an anti-angiogenic substance in a physiologically and pharmaceutically acceptable carrier, optionally with one or more excipients.

In a further aspect, the invention provides methods for treating a condition amenable to treatment by inhibiting angiogenesis by administering to a subject in need thereof an amount of an anti-angiogenesis agent effective for inhibiting angiogenesis.

Examples of the anti-angiogenesis agents used for inhibiting angiogenesis are also provided by the invention and include, but are not limited to, tetraiodothyroacetic acid (TETRAC), triiodothyroacetic acid (TRIAC), monoclonal antibody LM609, or combinations thereof. Such anti-angiogenesis agents can act at the cell surface to inhibit the pro-angiogenesis agents.

Cancer-Related New Blood Vessel Growth

Examples of the conditions amenable to treatment by inhibiting angiogenesis include, but are not limited to, primary or metastatic tumors. In such a method, compounds which inhibit the thyroid hormone-induced angiogenic effect are used to inhibit angiogenesis. Details of such a method is illustrated in Example 12.

Diabetic Retinopathy

Examples of the conditions amenable to treatment by inhibiting angiogenesis include, but are not limited to diabetic retinopathy, and related conditions. In such a method, compounds which inhibit the thyroid hormone-induced angiogenic effect are used to inhibit angiogenesis. Details of such a method is illustrated in Examples 8A and B.

It is known that proliferative retinopathy induced by hypoxia (rather than diabetes) depends upon alphaV ($\alpha$V) integrin expression (E Chavakis et al., Diabetologia 45:262-267, 2002). It is proposed herein that thyroid hormone action on a specific integrin alphaVbeta-3 ($\alpha$V$\beta$3) is permissive in the development of diabetic retinopathy. Integrin $\alpha$V$\beta$3 is identified herein as the cell surface receptor for thyroid hormone. Thyroid hormone, its analogs, and polymer conjugations, act via this receptor to induce angiogenesis.

Methods of Treatment

Thyroid hormone analogs, polymeric forms, and derivatives can be used in a method for promoting angiogenesis in a patient in need thereof. The method involves the co-administration of an effective amount of thyroid hormone analogs, polymeric forms, and derivatives in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine A.sub.2 agonists have been developed which have much longer half-lives, and which can be administered through other means. Thyroid hormone analogs, polymeric forms, and derivatives can be administered, for example, intravenously, oral, topical, intranasal administration.

In some embodiments, the thyroid hormone analogs, polymeric forms, and derivatives are administered via different means.

The amounts of the thyroid hormone, its analogs, polymeric forms, and derivatives required to be effective in stimulating angiogenesis will, of course, vary with the individual being treated and is ultimately at the discretion of the physician. The factors to be considered include the condition of the patient being treated, the efficacy of the particular adenosine A.sub.2 receptor agonist being used, the nature of the formulation, and the patient's body weight. Occlusion-treating dosages of thyroid hormone analogs or its polymeric forms, and derivatives are any dosages that provide the desired effect.

Formulations

The compounds described above are preferably administered in a formulation including thyroid hormone analogs or its polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound of formula (I), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the thyroid hormone analogs or its polymeric forms, and adenosine derivatives can be formulated into a liposome or microparticle, which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-.beta., basic fibroblast growth factor (FGF2), epithelial growth factor (EGF), transforming growth factors .alpha. and .beta. (TGF alpha. and beta.), nerve growth factor (NGF), platelet-derived growth factor (PDGF), and vascular endothelial growth factor/vascular permeability factor (VEGF/VPF)), antiviral, antibacterial, anti-inflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Materials & Methods

Reagents: All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. Fertilized chicken eggs were purchased from Charles River Laboratories, SPAFAS Avian Products & Services (North Franklin, Conn.). T4, 3,5,3'-triiodo-L-thyronine (T3), tetraiodothyroacetic acid (tetrac), T4 -agarose, and 6-N-propyl-2-thiouracil (PTU) were obtained from Sigma; PD 98059 from Calbiochem; and CGP41251 was a gift from Novartis Pharma (Basel, Switzerland). Polyclonal anti-FGF2 and monoclonal anti-β-actin were obtained from Santa Cruz Biotechnology and human recombinant FGF2 from Invitrogen. Polyclonal antibody to phosphorylated ERK1/2 was from New England Biolabs and goat anti-rabbit IgG from DAKO.

Chorioallantoic membrane (CAM) Model of Angiogenesis: In vivo Neovascularization was examined by methods described previously. 9-12 Ten-day-old chick embryos were purchased from SPAFAS (Preston, Conn.) and incubated at 37° C. with 55% relative humidity. A hypodermic needle was used to make a small hole in the shell concealing the air sac, and a second hole was made on the broad side of the egg, directly over an avascular portion of the embryonic membrane that was identified by candling. A false air sac was created beneath the second hole by the application of negative pressure at the first hole, causing the CAM to separate from the shell. A window approximately 1.0 cm 2 was cut in the shell over the dropped CAM with a small-crafts grinding wheel (Dremel, division of Emerson Electric Co.), allowing direct access to the underlying CAM. FGF2 (1 µg/mL) was used as a standard proangiogenic agent to induce new blood vessel branches on the CAM of 1 0-day-old embryos. Sterile disks of No. 1 filter paper (Whatman International) were pretreated with 3 mg/mL cortisone acetate and 1 mmol/L PTU and air dried under sterile conditions. Thyroid hormone, hormone analogues, FGF2 or control solvents, and inhibitors were then applied to the disks and the disks allowed to dry. The disks were then suspended in PBS and placed on growing CAMs. Filters treated with T4 or FGF2 were placed on the first day of the 3-day incubation, with antibody to FGF2 added 30 minutes later to selected samples as indicated. At 24 hours, the MAPK cascade inhibitor PD 98059 was also added to CAMs topically by means of the filter disks.

Microscopic Analysis of CAM Sections: After incubation at 37° C. with 55% relative humidity for 3 days, the CAM tissue directly beneath each filter disk was resected from control and treated CAM samples. Tissues were washed 3× with PBS, placed in 35-mm Petri dishes (Nalge Nunc), and examined under an SV6 stereomicroscope (Zeiss) at ×50 magnification. Digital images of CAM sections exposed to filters were collected using a 3-charge-coupled device color video camera system (Toshiba) and analyzed with Image-Pro software (Media Cybernetics). The number of vessel branch points contained in a circular region equal to the area of each filter disk were counted. One image was counted in each CAM preparation, and findings from 8 to 10 CAM preparations were analyzed for each treatment condition (thyroid hormone or analogues, FGF2, FGF2 antibody, PD 98059). In addition, each experiment was performed 3 times. The resulting angiogenesis index is the mean±SEM of new branch points in each set of samples.

FGF2 Assays: ECV304 endothelial cells were cultured in M199 medium supple mented with 10% fetal bovine serum. ECV304 cells ($10^6$ cells) were plated on 0.2% gel-coated 24-well plates in complete medium overnight, and the cells were then washed with serum-free medium and treated with T4 or T3 as indicated. After 72 hours, the supernatants were harvested and assays for FGF performed without dilution using a commercial ELISA system (R&D Systems).

MAPK Activation: ECV304 endothelial cells were cultured in M199 medium with 0.25% hormone-depleted serum 13 for 2 days. Cells were then treated with T4 ($10^{-7}$ mol/L) for 15 minutes to 6 hours. In additional experiments, cells were treated with T4 or FGF2 or with T4 in the presence of PD 98059 or CGP41251. Nuclear fractions were pre-pared from all samples by our method reported previously, the proteins separated by polyacrylamide gel electrophoresis, and transferred to membranes for immunoblotting with antibody to phosphorylated ERK1/2. The appearance of nuclear phosphorylated ERK1/2 signifies activation of these MAPK isoforms by T4.

Reverse Transcription-Polymerase Chain Reaction: Confluent ECV304 cells in 10-cm plates were treated with T4 ($10^{-7}$ mol/L) for 6 to 48 hours and total RNA extracted using guanidinium isothiocyanate (Biotecx Laboratories). RNA (1 µg) was subjected to reverse transcription-polymerase chain reaction (RT-PCR) using the Access RT-PCR system (Promega). Total RNA was reverse transcribed into cDNA at 48° C. for 45 minutes, then denatured at 94° C. for 2 minutes. Second-strand synthesis and PCR amplification were performed for 40 cycles with denaturation at 94° C. for 30 s, annealing at 60° C. for 60 s, and extension at 68° C. for 120 s, with final ex-tension for 7 minutes at 68° C. after completion of all cycles. PCR primers for FGF2 were as follows: FGF2 sense strand 5'-TGGTATGTGGCACTGAAACG-3' (SEQ ID NO:1), antisense strand 5' CTCAATGACCTGGCGAAGAC-3' (SEQ ID NO:2); the length of the PCR product was 734 bp. Primers for GAPDH included the sense strand 5'-AAGGTCATCCCTGAGCTGAACG-3' (SEQ ID NO:3), and antisense strand 5'-GGGTGTCGCTGTTGAAGTCAGA-3' (SEQ ID NO:4); the length of the PCR product was 218 bp. The products of RT-PCR were separated by electrophoresis on 1.5% agarose gels and visualized with ethidium bromide. The target bands of the gel were quantified using Labimage software (Kapelan), and the value for [FGF2/GAPDH]×10 calculated for each time point.

Statistical Analysis: Statistical analysis was performed by 1-way ANOVA comparing experimental with control samples.

In vivo angiogenesis in Matrigel $FGF_2$ or Cancer cell lines implant in mice: In Vivo Murine Angiogenesis Model: The murine matrigel model will be conducted according to previously described methods (Grant et al., 1991; Okada et al., 1995) and as implemented in our laboratory (Powel et al., 2000). Briefly, growth factor free matrigel (Becton Dickinson, Bedford Mass.) will be thawed overnight at 4° C. and placed on ice. Aliquots of matrigel will be placed into cold polypropylene tubes and FGF2, thyroid hormone analogs or cancer cells ($1 \times 10^6$ cells) will be added to the matrigel. Matrigel with Saline, FGF2, thyroid hormone analogs or cancer cells will be subcutaneously injected into the ventral midline of the mice. At day 14, the mice will be sacrificed and the solidified gels will be resected and analyzed for presence of new vessels. Compounds A-D will be injected subcutaneously at different doses. Control and experimental gel implants will be placed in a micro centrifuige tube containing 0.5 ml of cell lysis solution (Sigma, St. Louis, Mo.) and crushed with a pestle. Subsequently, the tubes will be allowed to incubate overnight at 4° C. and centrifuged at 1,500×g for 15 minutes on the following day. A 200 µl aliquot of cell lysate will be added to 1.3 ml of Drabkin's reagent solution (Sigma, St. Louis, Mo.) for each sample. The solution will be analyzed on a spectrophotometer at a 540 nm. The absorption of light is proportional to the amount of hemoglobin contained in the sample.

Figure 8:
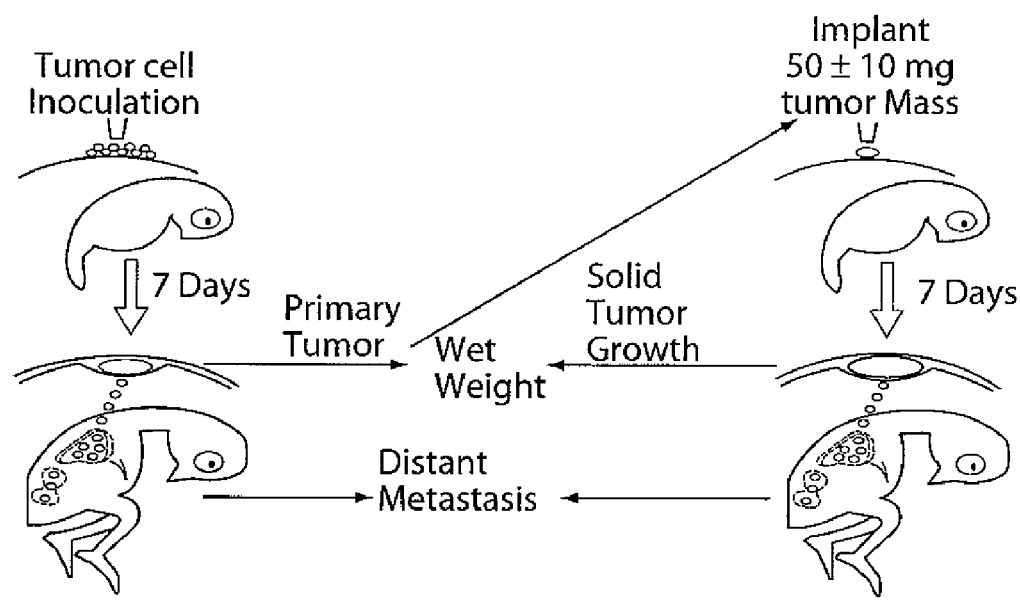
FIG. 8. 7 Day Chick Embryo Tumor Growth Model. Illustration of the Chick Chorioallantoic Membrane (CAM) model of tumor implant.
Figure 9:
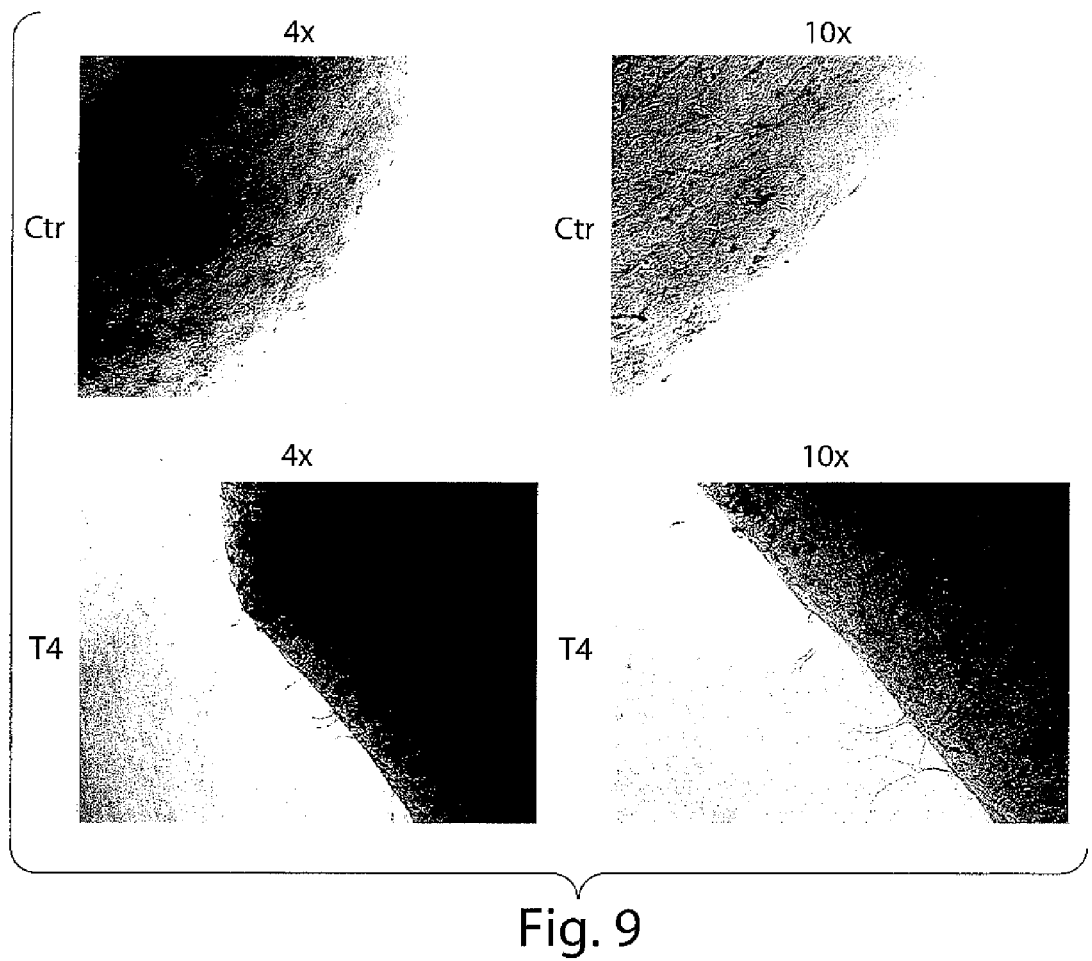
FIG. 9. T4 Stimulates 3D Wound Healing. Photographs of human dermal fibroblast cells exposed to T4 and control, according to the 3D Wound Healing Assay described herein.
Figure 10:
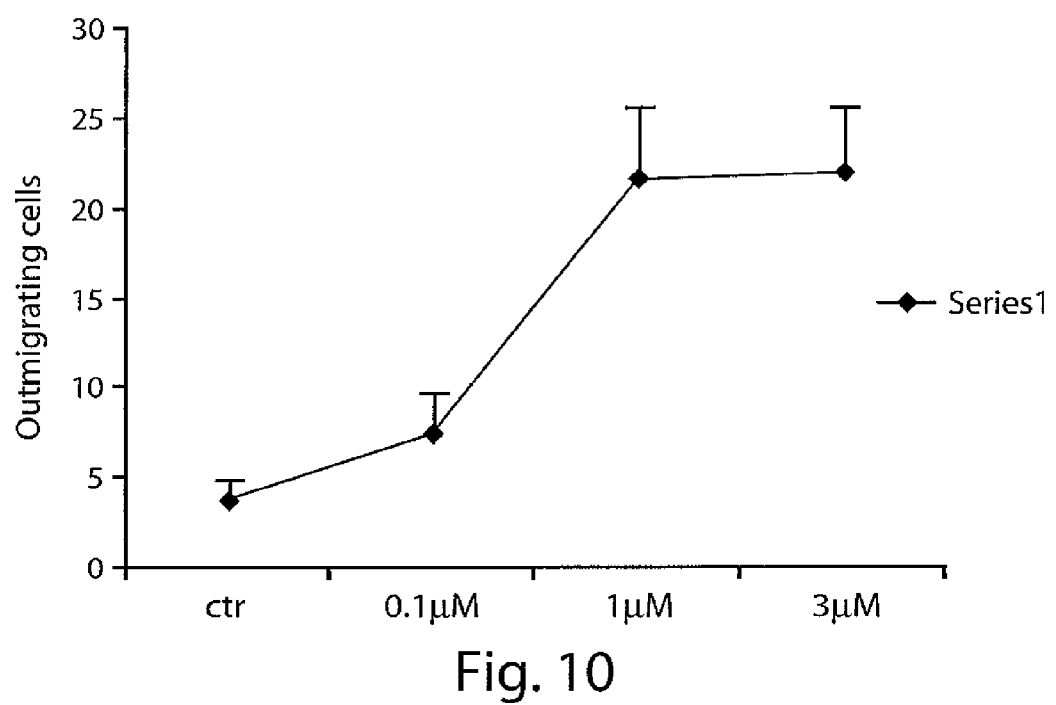
FIG. 10. T4 Dose-Dependently Increases Wound Healing, Day 3. As indicated by the graph, T4 increases wound healing (measured by outmigrating cells) in a dose-dependent manner between concentrations of 0.1 μM and 1.0 μM. This same increase is not seen in concentrations of T4 between 1.0 μM and 3.0 μM.
Figure 11A:
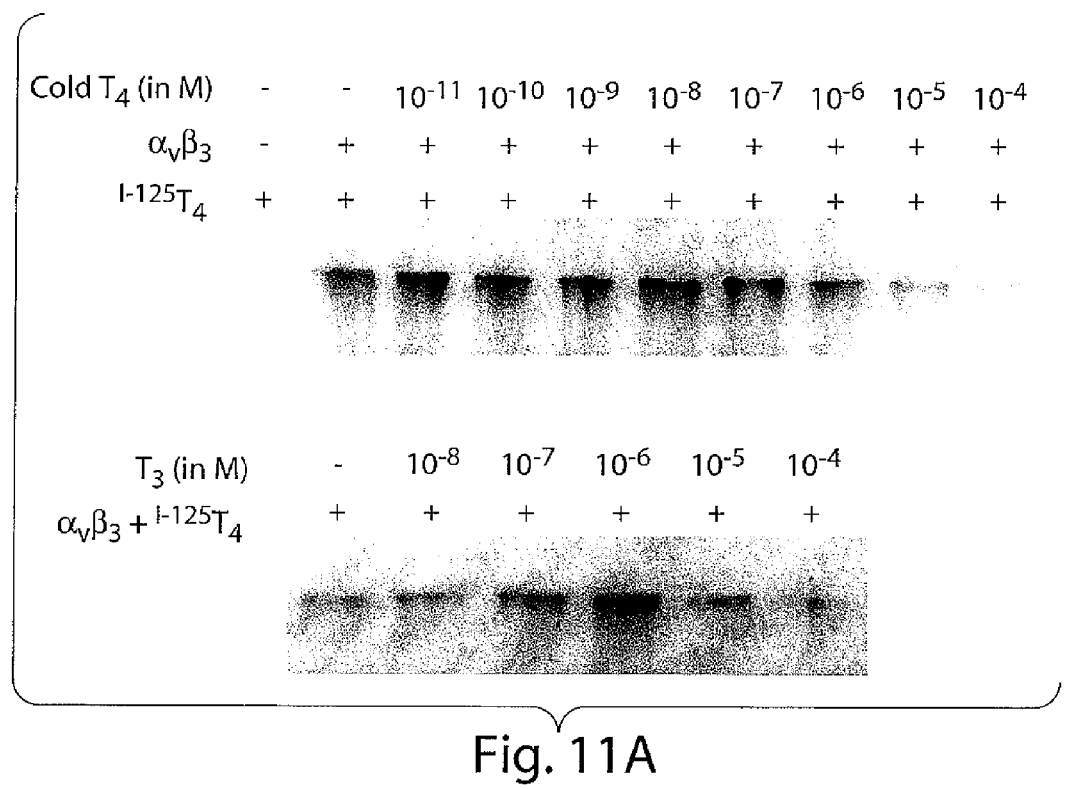
FIG. 11. Effect of unlabeled $T_4$ and $T_3$ on $^{I-125}$-$T_4$ binding to purified integrin. Unlabeled $T_4$ ($10^{-4}$M to $10^{-11}$M) or $T_3$ ($10^{-4}$M to $10^{-8}$M) were added to purified αVβ3 integrin (2 μg/sample) and allowed to incubate for 30 min. at room temperature. Two microcuries of I-125 labeled $T_4$ was added to each sample. The samples were incubated for 20 min. at room temperature, mixed with loading dye, and run on a 5% Native gel for 24 hrs. at 4° C. at 45 mÅ. Following electrophoresis, the gels were wrapped in plastic wrap and exposed to film. $^{I-125}$-$T_4$ binding to purified αVβ3 is unaffected by unlabeled $T_4$ in the range of $10^{-11}$M to $10^{-7}$M, but is competed out in a dose-dependent manner by unlabeled $T_4$ at a concentration of $10^{-6}$M. Hot $T_4$ binding to the integrin is almost completely displaced by $10^{-4}$M unlabeled $T_4$. $T_3$ is less effective at competing out $T_4$ binding to αVβ3, reducing the signal by 11%, 16%, and 28% at $10^{-6}$M, $10^{-5}$M, and $10^{-4}$M $T_3$, respectively.
Figure 11B:
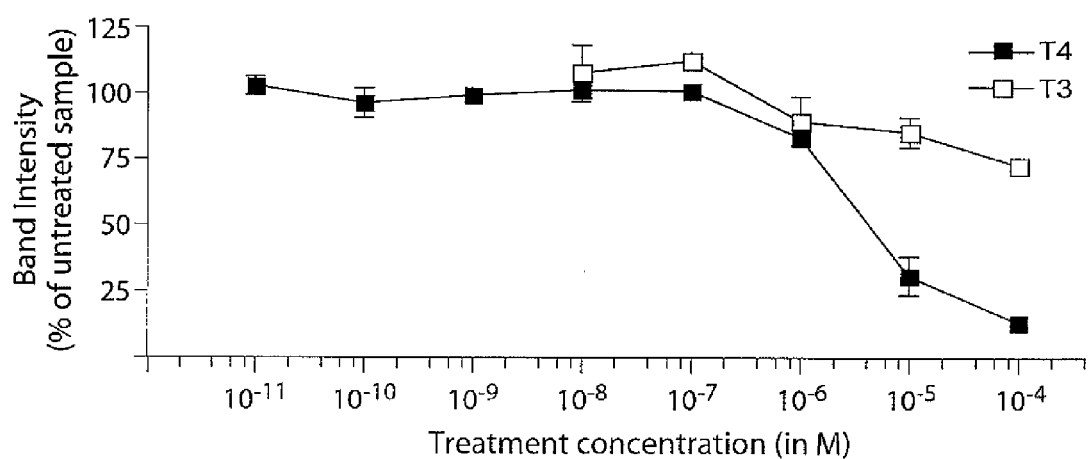
Figure 12A:
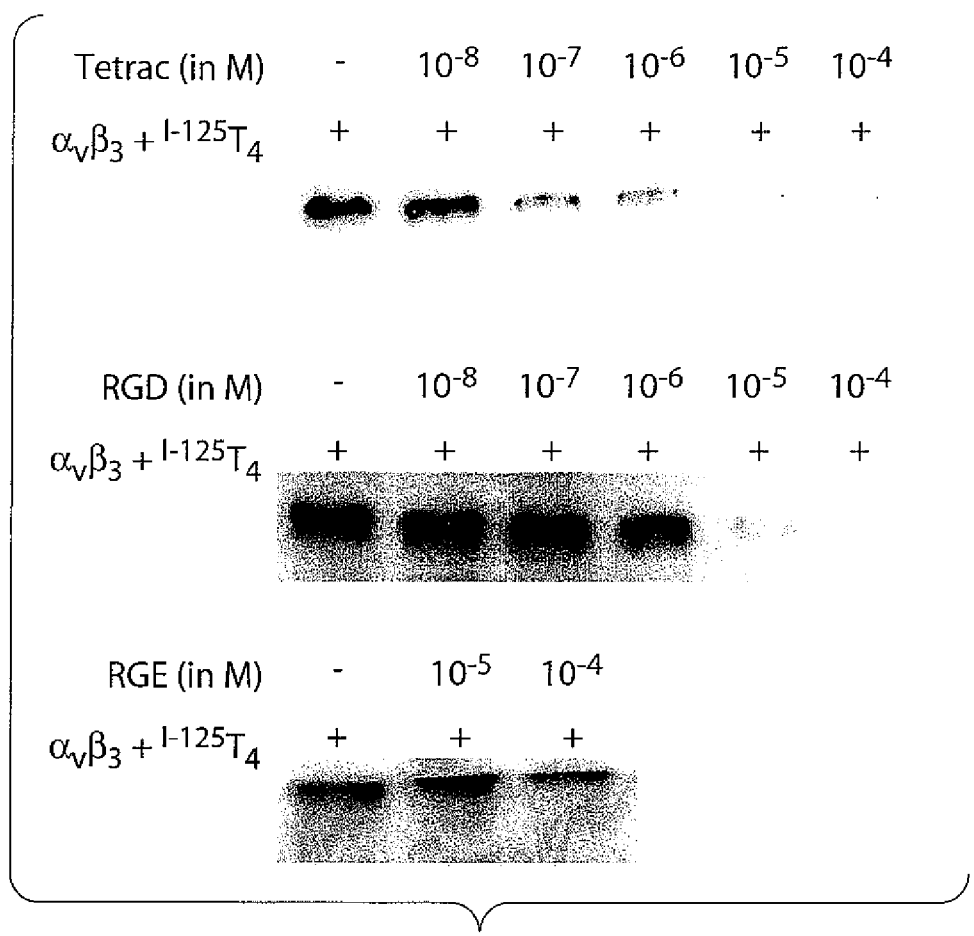
FIG. 12. Tetrac and an RGD containing peptide, but not an RGE containing peptide compete out $T_4$ binding to purified αVβ3. A) Tetrac addition to purified αVβ3 reduces $^{I-125}$-labeled $T_4$ binding to the integrin in a dose dependent manner. $10^{-8}$M tetrac is ineffective at competing out hot $T_4$ binding to the integrin. The association of $T_4$ and αVβ3 was reduced by 38% in the presence of $10^{-7}$M tetrac and by 90% with $10^{-5}$M tetrac. Addition of an RGD peptide at $10^{-5}$M competes out $T_4$ binding to αVβ3. Application of $10^{-5}$M and $10^{-4}$M RGE peptide, as a control for the RGD peptide, was unable to diminish hot $T_4$ binding to purified αVβ3. B) Graphical representation of the tetrac and RGD data from panel A. Data points are shown as the mean±S.D. for 3 independent experiments.
Figure 12B:
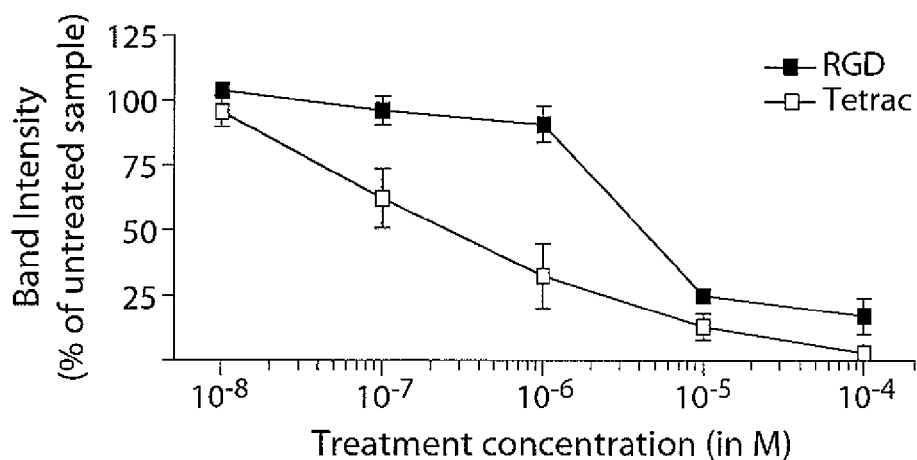
Figure 13A:
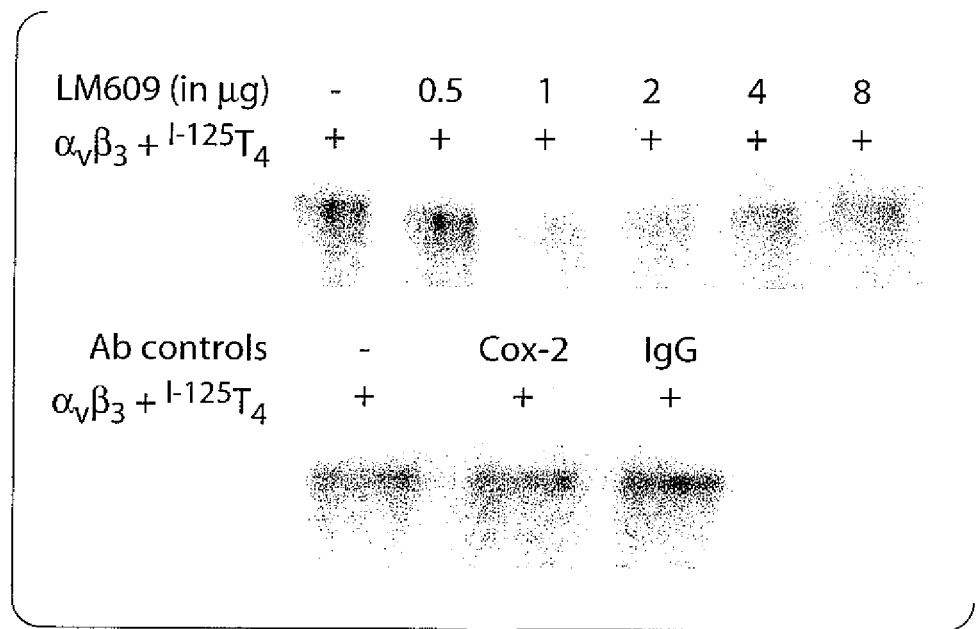
FIG. 13. Effects of the monoclonal antibody LM609 on $T_4$ binding to αVβ3. A) LM609 was added to αVβ3 at the indicated concentrations. One μg of LM609 per sample reduces $^{I-125}$-labeled $T_4$ binding to the integrin by 52%. Maximal inhibition of $T_4$ binding to the integrin is reached when concentrations of LM609 are 2 μg per sample and is maintained with antibody concentrations as high as 8 μg. As a control for antibody specificity, 10 μg/sample Cox-2 mAB and 10 μg/sample mouse IgG were added to αVβ3 prior to incubation with $T_4$. B) Graphical representation of data from panel A. Data points are shown as the mean±S.D. for 3 independent experiments.
Figure 13B:
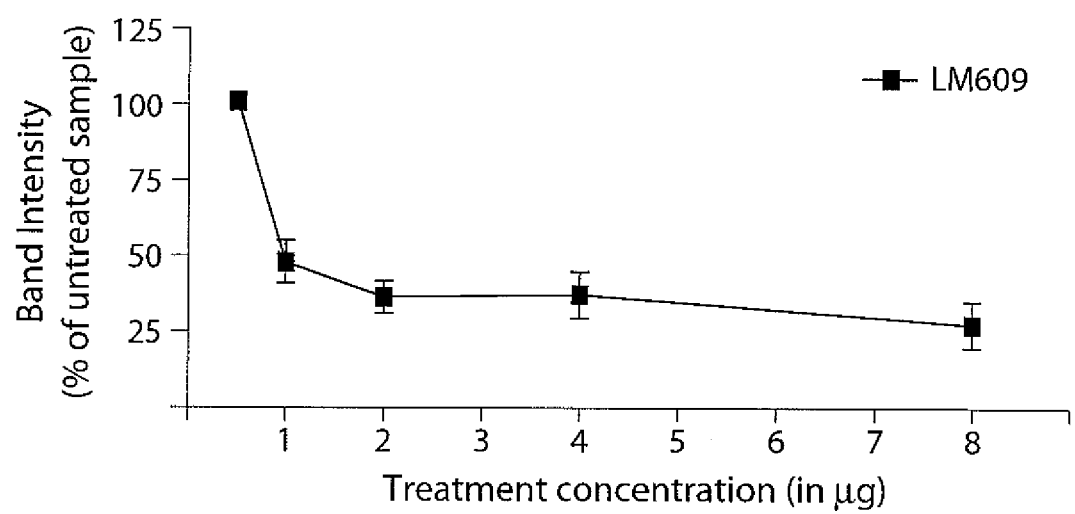
Figure 14A:
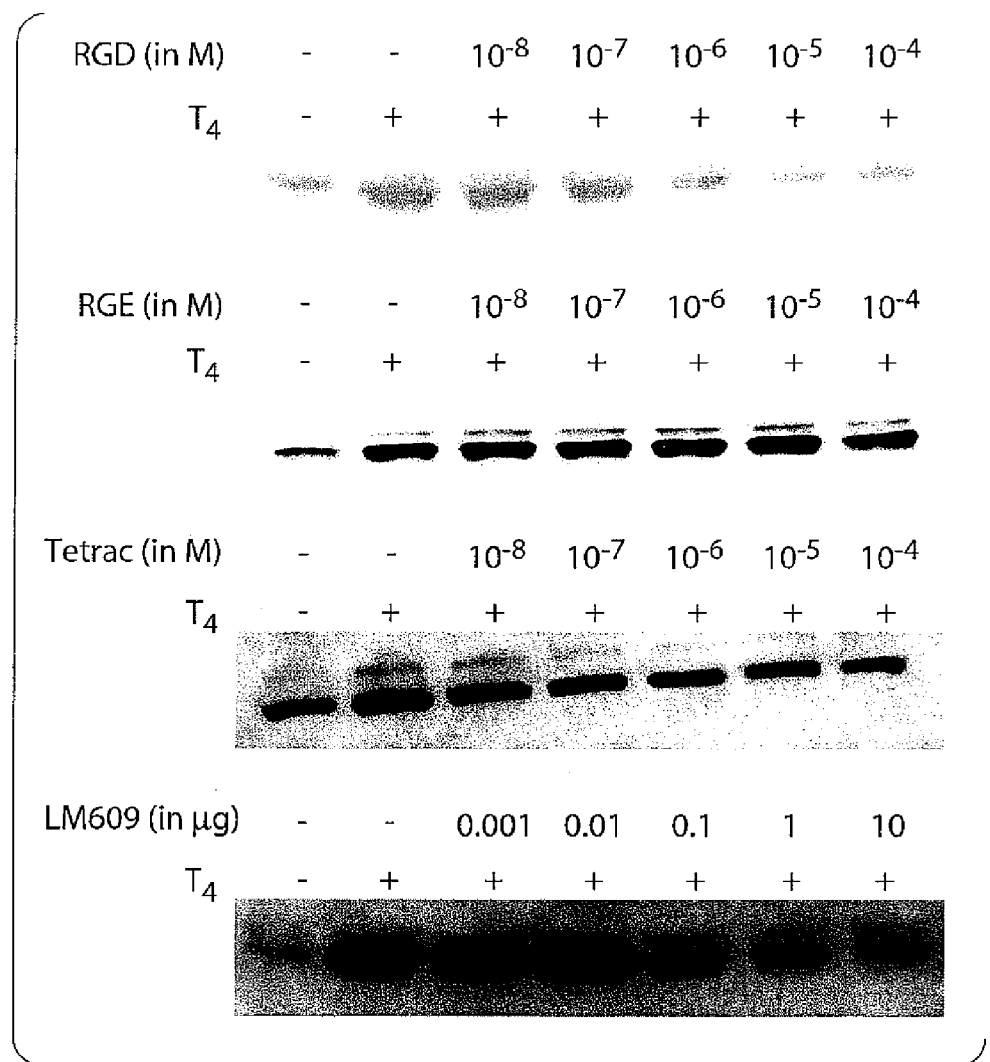
FIG. 14. Effect of RGD, RGE, tetrac, and the mAB LM609 on $T_4$-induced MAPK activation. A) CV-1 cells (50-70% confluency) were treated for 30 min. with $10^{-7}$M $T_4$ ($10^{-7}$M total concentration, $10^{-10}$M free concentration. Selected samples were treated for 16 hrs with the indicated concentrations of either an RGD containing peptide, an RGE containing peptide, tetrac, or LM609 prior to the addition of $T_4$. Nuclear proteins ere separated by SDS-PAGE and immunoblotted with anti-phospho-MAPK (pERK1/2) antibody. Nuclear accumulation of pERK1/2 is diminished in samples treated with $10^{-6}$ M RGD peptide or higher, but not significantly altered in samples treated with $10^{-4}$ M RGE. pERK1/2 accumulation is decreased 76% in CV1 cells treated with $10^{-6}$M tetrac, while $10^{-5}$M and higher concentrations of tetrac reduce nuclear accumulation of pERK1/2 to levels similar to the untreated control samples. The monoclonal antibody to αVβ3 LM609 decrease accumulation of activated MAPK in the nucleus when it is applied to CV1 cultures a concentration of 1 µg/ml. B) Graphical representation of the data for RGD, RGE, and tetrac shown in panel A. Data points represent the mean±S.D. for 3 separate experiments.
Figure 14B:
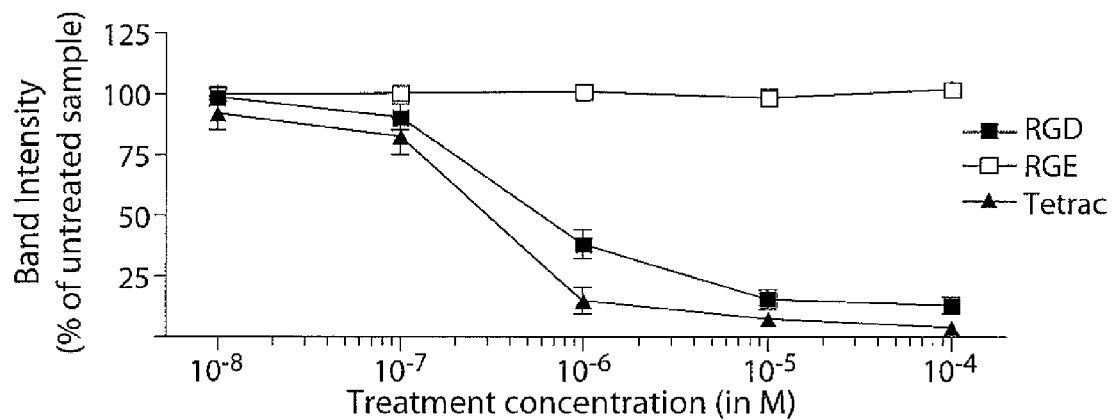
Figure 15A:
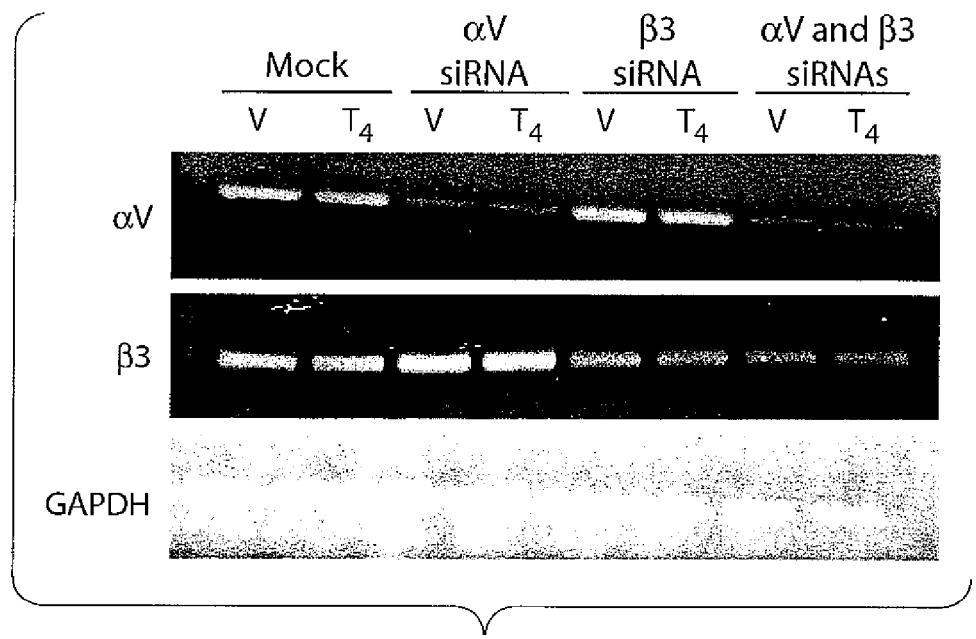
FIG. 15. Effects of siRNA to αV and β3 on $T_4$ induced MAPK activation. CV1 cells were transfected with siRNA (100 nM final concentration) to αV, β3, or αV and β3 together. Two days after transfection, the cells were treated with $10^{-7}$M $T_4$. A) RT-PCR was performed from RNA isolated from each transfection group to verify the specificity and functionality of each siRNA. B) Nuclear proteins from each transfection were isolated and subjected to SDS-PAGE.
Figure 15B:
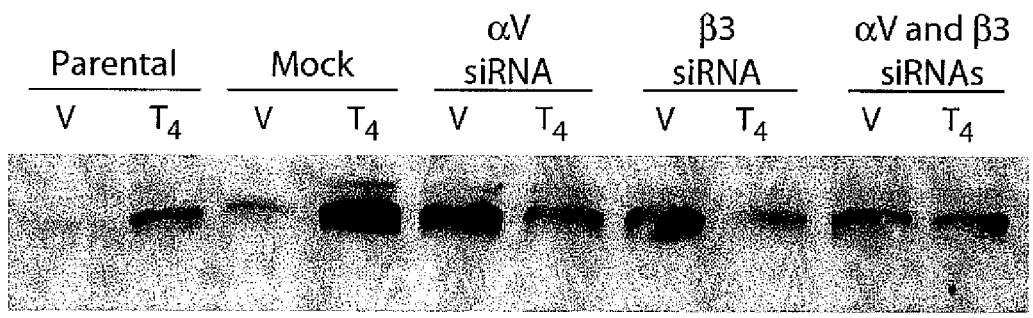

Tumor growth and metastasis—Chick Chorioallantoic Membrane (CAM) model of tumor implant: The protocol is as previously described (Kim et al., 2001). Briefly, $1 \times 10^7$ tumor cells will be placed on the surface of each CAM (7 day old embryo) and incubated for one week. The resulting tumors will be excised and cut into 50 mg fragments. These fragments will be placed on additional 10 CAMs per group and treated topically the following day with 25 µl of compounds (A-D) dissolved in PBS. Seven days later, tumors will then be excised from the egg and tumor weights will be determined for each CAM. FIG. 8 is a diagrammatic sketch showing the steps involved in the in vivo tumor growth model in the CAM.

The effects of TETRAC, TRIAC, and thyroid hormone antagonists on tumor growth rate, tumor angiogenesis, and tumor metastasis of cancer cell lines can be determined.

Tumor growth and metastasis—Tumor Xenograft model in mice: The model is as described in our publications by Kerr et al., 2000; Van Waes et al., 2000; Ali et al., 2001; and Ali et al., 2001, each of which is incorporated herein by reference in its entirety). The anti-cancer efficacy for TETRAC, TRIAC, and other thyroid hormone antagonists at different doses and against different tumor types can be determined and compared.

Tumor growth and metastasis—Experimental Model of Metastasis: The model is as described in our recent publications (Mousa, 2002; Amirkhosravi et al., 2003a and 2003b, each of which is incorporated by reference herein in its entirety). Briefly, B16 murine malignant melanoma cells (ATCC, Rockville, Md.) and other cancer lines will be cultured in RPMI 1640 (Invitrogen, Carlsbad, Calif.), supplemented with 10% fetal bovine serum, penicillin and streptomycin (Sigma, St. Louis, Mo.). Cells will be cultured to 70% confluency and harvested with trypsin-EDTA (Sigma) and washed twice with phosphate buffered saline (PBS). Cells will be re-suspended in PBS at a concentration of either $2.0\times10^5$ cells/ml for experimental metastasis. Animals: C57/BL6 mice (Harlan, Indianapolis, Ind.) weighing 18-21 grams will be used for this study. All procedures are in accordance with IACUC and institutional guidelines. The anti-cancer efficacy for TETRAC, TRIAC, and other thyroid hormone antagonists at different doses and against different tumor types can be determined and compared.

Effect of Thyroid Hormone Analogues on Angiogenesis.

T4 induced significant increase in angiogenesis index (fold increase above basal) in the CAM model. T3 at 0.001-1.0 μM or T4 at 0.1-1.0 μM achieved maximal effect in producing 2-2.5 fold increase in angiogenesis index as compared to 2-3 fold increase in angiogenesis index by 1 μg of FGF2 (Table 1 and FIGS. 1a and 1b). The effect of T4 in promoting angiogenesis (2-2.5 fold increase in angiogenesis index) was achieved in the presence or absence of PTU, which inhibit T4 to T3 conversion. T3 itself at 91-100 nM)-induced potent pro-angiogenic effect in the CAM model. T4 agarose produced similar pro-angiogenesis effect to that achieved by T4. The pro-angiogenic effect of either T4 or T4-agarose was 100% blocked by TETRAC or TRIAC.

Enhancement of Pro-angiogenic Activity of FGF2 by Submaximal Concentrations of $T_4$.

The combination of T4 and FGF2 at sub-maximal concentrations resulted in an additive increase in the angiogenesis index up to the same level like the maximal pro-angiogenesis effect of either FGF2 or T4 (FIG. 2).

Figures 3A, 3B:
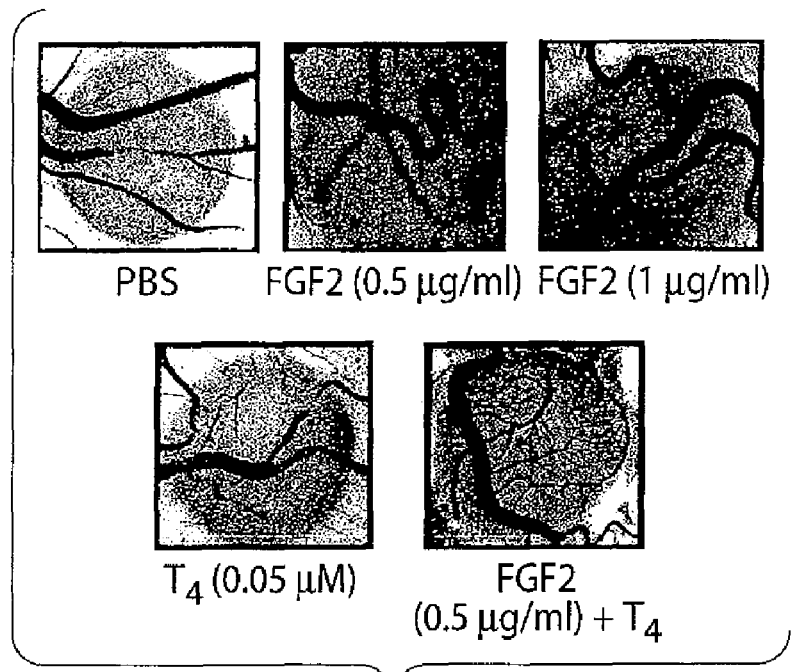
FIG. 3. Comparison of the proangiogenic effects of FGF2 and T4. A, Tandem effects of T4 (0.05 µmol/L) and FGF2 (0.5 µg/mL) in submaximal concentrations are additive in the CAM assay and equal the level of angiogenesis seen with FGF2 (1 µg/mL in the absence of T4). B, Summary of results from 3 experiments that examined actions of FGF2 and T4 in the CAM assay (means±SEM) as in A. *$P<0.05$; **$P<0.001$, comparing results of treated samples with those of PBS-treated control samples in 3 experiments.

Effects of MAPK cascade inhibitors on the pro-angiogenic actions of $T_4$ and FGP n the CAM model. The pro-angiogenesis effect of either T4 or FGF2 was totally blocked by PD 98059 at 0.8-8 μg (FIG. 3).

Figures 4A, 4B:
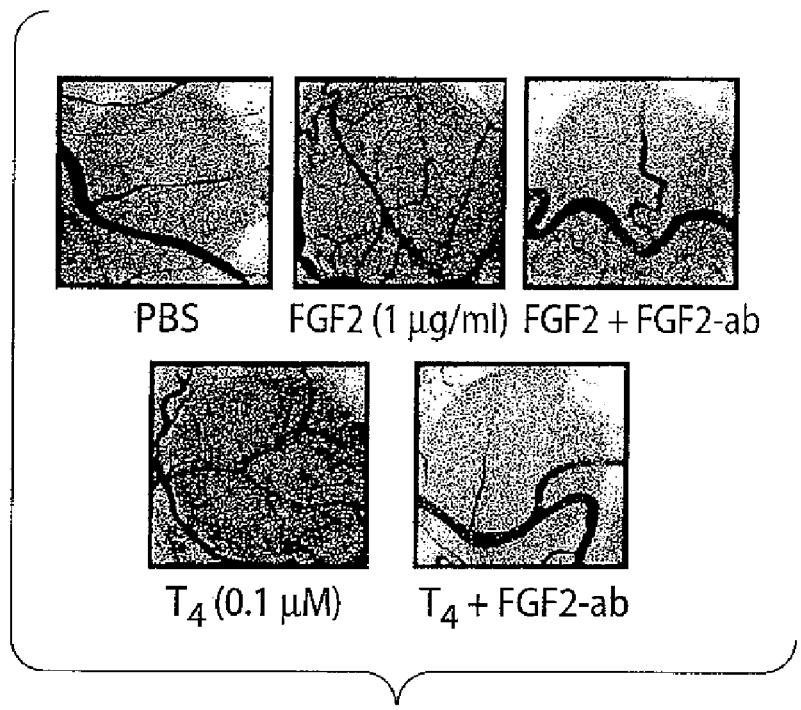
FIG. 4. Effect of anti-FGF2 on angiogenesis caused by T4 or exogenous FGF2. A, FGF2 caused a 2-fold increase in angiogenesis in the CAM model in 3 experiments, an effect inhibited by antibody (ab) to FGF2 (8 µg). T4 also stimulated angiogenesis 1.5-fold, and this effect was also blocked by FGF2 antibody, indicating that the action of thyroid hormone in the CAM model is mediated by an autocrine/paracrine effect of FGF2 because T4 and T3 cause FGF2 release from cells in the CAM model (Table 1). We have shown previously that a nonspecific IgG antibody has no effect on angiogenesis in the CAM assay. B, Summary of results from 3 CAM experiments that studied the action of FGF2-ab in the presence of FGF2 or T4. *P<0.01; **P<0.001, indicating significant effects in 3 experiments studying the effects of thyroid hormone and FGF2 on angiogenesis and loss of these effects in the presence of antibody to FGF2.

Effects of specific integrin αvβ3 antagonists on the pro-angiogenic actions of $T_4$ and FGf2 n the CAM model. The pro-angiogenesis effect of either T4 or FGF2 was totally blocked by the specific monoclonal antibody LM609 at 10 μg (FIGS. 4a and 4b).

The CAM assay has been used to validate angiogenic activity of a variety of growth factors and other promoters or inhibitors of angiogenesis (2-9). In the present studies, $T_4$ in physiological concentrations was shown to be pro-angiogenic, with comparable activity to that of FGF2. The presence of PTU did not reduce the effect of $T_4$, indicating that de-iodination of $T_4$ to generate $T_3$ was not a prerequisite in this model. Because the appearance of new blood vessel growth in this model requires several days, we assumed that the effect of thyroid hormone was totally dependent upon the interaction of the nuclear receptor for thyroid hormone (TR). Actions of iodothyronines that require intranuclear complexing of TR with its natural ligand, $T_3$, are by definition, genomic, and culminate in gene expression. On the other hand, the preferential response of this model system to $T_4$-rather than $T_3$, the natural ligand of TR raised the possibility that angiogenesis might be initiated non-nomically at the plasma membrane by $T_4$ and culminate in effects that require gene transcription. Non-genomic actions of $T_4$ have been widely described, are usually initiated at the plasma membrane and may be mediated by signal transduction pathways. They do not require intranuclear ligand binding of iodothyronine and TR, but may interface with or modulate gene transcription. Non-genomic actions of steroids have also been well-described and are known to interface with genomic actions of steroids or of other compounds. Experiments carried out with $T_4$ and tetrac or with agarose-$T_4$ indicated that the pro-angiogenic effect of $T_4$ indeed very likely was initiated at the plasma membrane. We have shown elsewhere that tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used by us and others to examine models for possible cell surface-initiated actions of the hormone.

These results suggest that another consequence of activation of MAPK by thyroid hormone is new blood vessel growth. The latter is initiated nongenomically, but of course requires a consequent complex gene transcription program.

The ambient concentrations of thyroid hormone are relatively stable. The CAM model, at the time we tested it, was thyroprival and thus may be regarded as a system, which does not reproduce the intact organism. We propose that circulating levels of $T_4$ serve, with a variety of other regulators, to modulate the sensitivity of vessels to endogenous angiogenic factors, such as VEGF and FGF2.

The invention will be further illustrated in the following non-limiting examples.

EXAMPLES

Example 1

Effect of Thyroid Hormone on Angiogenesis

As seen in FIG. 1A and summarized in FIG. 1B, both L-T4 and L-T3 enhanced angiogenesis in the CAM assay. T4, 25 at a physiologic total concentration in the medium of 0.1 μmol/L, increased blood vessel branch formation by 2.5-fold (P<0.001). T3 (1 nmol/L) also stimulated angiogenesis 2-fold. The possibility that T4 was only effective because of conversion of T4 to T3 by cellular 5'-monodeiodinase was ruled out by the finding that the deiodinase inhibitor PTU had no inhibitory effect on angiogenesis produced by T4. PTU was applied to all filter disks used in the CAM model. Thus, T4 and T3 promote new blood vessel branch formation in a CAM model that has been standardized previously for the assay of growth factors.

Example 2

Effects of T4-Agarose and Tetrac

We have shown previously that T4-agarose stimulates cellular signal transduction pathways initiated at the plasma membrane in the same manner as T4 and that the actions of T4 and T4-agarose are blocked by a deaminated iodothyronine analogue, tetrac, which is known to inhibit binding of T4 to plasma membranes. In the CAM model, the addition of tetrac (0.1 μmol/L) inhibited the action of T4 (FIG. 2A), but tetrac alone had no effect on angiogenesis (FIG. 2C). The action of T4-agarose, added at a hormone concentration of 0.1 μmol/L, was comparable to that of T4 in the CAM model (FIG. 2B), and the effect of T4-agarose was also inhibited by the action of tetrac (FIG. 2B; summarized in 2C).

Example 3

Enhancement of Proangiogenic Activity of FGF2 by a Submaximal Concentration of T4

Angiogenesis is a complex process that usually requires the participation of polypeptide growth factors. The CAM assay requires at least 48 hours for vessel growth to be manifest; thus, the apparent plasma membrane effects of thyroid hormone in this model are likely to result in a complex transcriptional response to the hormone. Therefore, we determined whether FGF2 was involved in the hormone response and whether the hormone might potentiate the effect of subphysiologic levels of this growth factor. T4 (0.05 μmol/L) and FGF2 (0.5 μg/mL) individually stimulated angiogenesis to a modest degree (FIG. 3). The angiogenic effect of this submaximal concentration of FGF2 was enhanced by a subphysiologic concentration of T4 to the level caused by 1.0 μg FGF2 alone. Thus, the effects of submaximal hormone and growth factor concentrations appear to be additive. To define more precisely the role of FGF2 in thyroid hormone stimulation of angiogenesis, a polyclonal antibody to FGF2 was added to the filters treated with either FGF2 or T4, and angiogenesis was measured after 72 hours. FIG. 4 demonstrates that the FGF2 antibody inhibited angiogenesis stimulated either by FGF2 or by T4 in the absence of exogenous FGF2, suggesting that the T4 effect in the CAM assay was mediated by increased FGF2 expression. Control IgG antibody has no stimulatory or inhibitory effect in the CAM assay.

Example 4

Stimulation of FGF2 Release From Endothelial Cells by Thyroid Hormone

Levels of FGF2 were measured in the media of ECV304 endothelial cells treated with either T4 (0.1 μmol/L) or T3 (0.01 μmol/L) for 3 days. As seen in the Table 2, T3 stimulated FGF2 concentration in the medium 3.6-fold, whereas T4 caused a 1.4-fold increase. This finding indicates that thyroid hormone may enhance the angiogenic effect of FGF2, at least in part, by increasing the concentration of growth factor available to endothelial cells.

TABLE 2

Effect of T4 and T3 on Release of FGF2 From ECV304 Endothelial Cells

| Cell Treatment | FGF2 (pg/mL/$10^6$ cells) |
| --- | --- |
| Control | 27.7 ± 3.1 |
| T3 (0.01 μmol/L) | 98.8 ± 0.5* |
| T3 + PD 98059 (2 μmol/L) | 28.4 ± 3.2 |
| T3 + PD 98059 (20 μmol/L) | 21.7 ± 3.5 |
| T4 (0.1 μmol/L) | 39.2 ± 2.8† |
| T4 + PD 98059 (2 μmol/L) | 26.5 ± 4.5 |
| T4 + PD 98059 (20 μmol/L) | 23.2 ± 4.8 |

*$P < 0.001$, comparing T3-treated samples with control samples by ANOVA;
†$P < 0.05$, comparing T4-treated samples with control samples by ANOVA.

Example 5

Role of the ERK1/2 Signal Transduction Pathway in Stimulation of Angiogenesis by Thyroid Hormone and FGF2

A pathway by which T4 exerts a nongenomic effect on cells is the MAPK signal transduction cascade, specifically that of ERK1/2 activation. We know that T4 enhances ERK1/2 activation by epidermal growth factor. The role of the MAPK pathway in stimulation by thyroid hormone of FGF2 expression was examined by the use of PD 98059 (2 to 20 μmol/L), an inhibitor of ERK1/2 activation by the tyrosine-threonine kinases MAPK kinase-1 (MEK1) and MEK2. The data in the Table demonstrate that PD 98059 effectively blocked the increase in FGF2 release from ECV304 endothelial cells treated with either T4 or T3. Parallel studies of ERK1/2 inhibition were performed in CAM assays, and representative results are shown in FIG. 5. A combination of T3 and T4, each in physiologic concentrations, caused a 2.4-fold increase in blood vessel branching, an effect that was completely blocked by 3 μmol/L PD 98059 (FIG. 5A). FGF2 stimulation of branch formation (2.2-fold) was also effectively blocked by this inhibitor of ERK1/2 activation (FIG. 5B). Thus, the proangiogenic effect of thyroid hormone begins at the plasma membrane and involves activation of the ERK1/2 pathway to promote FGF2 release from endothelial cells. ERK1/2 activation is again required to transduce the FGF2 signal and cause new blood vessel formation.

Example 6

Action of Thyroid Hormone and FGF2 on MAPK Activation

Figure 6A:
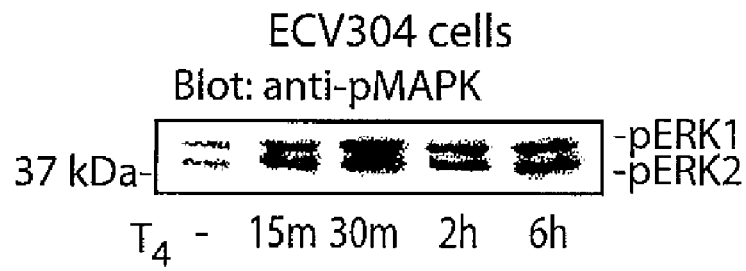
FIG. 6. T4 and FGF2 activate MAPK in ECV304 endothelial cells. Cells were prepared in M199 medium with 0.25% hormone-depleted serum and treated with T4 (0.1 μmol/L) for 15 minutes to 6 hours. Cells were harvested and nuclear fractions prepared as described previously. Nucleoproteins, separated by gel electrophoresis, were immunoblotted with antibody to phosphorylated MAPK (PERK1 and pERK2, 44 and 42 kDa, respectively), followed by a second antibody linked to a luminescence-detection system. A β-actin immunoblot of nuclear fractions serves as a control for gel loading in each part of this figure. Each immunoblot is representative of 3 experiments. A, T4 causes increased phosphorylation and nuclear translocation of ERK1/2 in ECV304 cells. The effect is maximal in 30 minutes, although the effect remains for ≧6 hours. B, ECV304 cells were treated with the ERK1/2 activation inhibitor PD 98059 (PD; 30 μmol/L) or the PKC inhibitor CGP41251 (CGP; 100 nmol/L) for 30 minutes, after which $10^{-7}$ M T4 was added for 15 minutes to cell samples as shown. Nuclei were harvested, and this representative experiment shows increased phosphorylation (activation) of ERK1/2 by T4 (lane 4), which is blocked by both inhibitors (lanes 5 and 6), suggesting that PKC activity is a requisite for MAPK activation by T4 in endothelial cells. C, ECV304 cells were treated with either T4 ($10^{-7}$ mol/L), FGF2 (10 ng/mL), or both agents for 15 minutes. The figure shows pERK1/2 accumulation in nuclei with either hormone or growth factor treatment and enhanced nuclear pERK1/2 accumulation with both agents together.
Figure 6B:
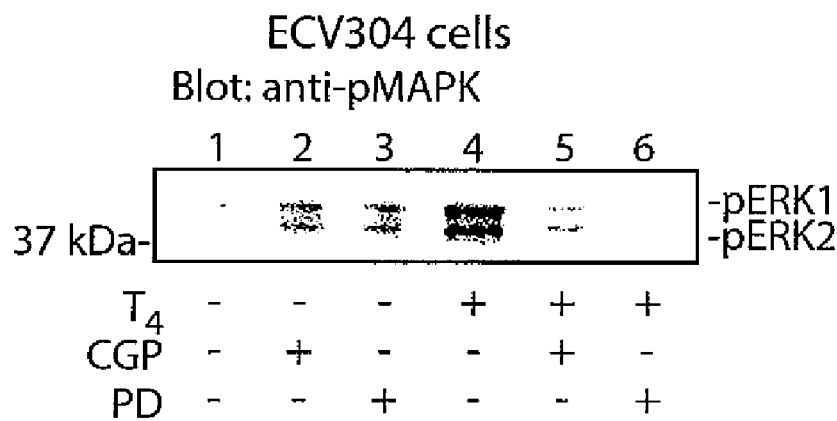
Figure 6C:
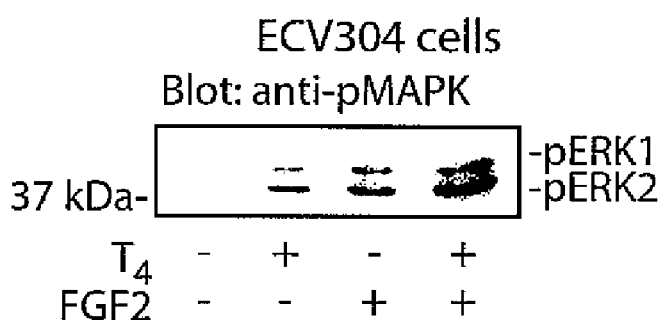

Stimulation of phosphorylation and nuclear translocation of ERK1/2 MAPKs was studied in ECV304 cells treated with T4 ($10^{-7}$ mol/L) for 15 minutes to 6 hours. The appearance of phosphorylated ERK1/2 in cell nuclei occurred within 15 minutes of T4 treatment, reached a maximal level at 30 minutes, and was still apparent at 6 hours (FIG. 6A). This effect of the hormone was inhibited by PD 98059 (FIG. 6B), a result to be expected because this compound blocks the phosphorylation of ERK1/2 by MAPK kinase. The traditional protein kinase C (PKC)-α, PKC-β, and PKC-γ inhibitor CGP41251 also blocked the effect of the hormone on MAPK activation in these cells, as we have seen with T4 in other cell lines. Thyroid hormone enhances the action of several cytokines and growth factors, such as interferon-γ13 and epidermal growth factor. In ECV304 cells, T4 enhanced the MAPK activation caused by FGF2 in a 15-minute co incubation (FIG. 6C). Applying observations made in ECV304 cells to the CAM model, we propose that the complex mechanism by which the hormone induces angiogenesis includes endothelial cell release of FGF2 and enhancement of the autocrine effect of released FGF2 on angiogenesis.

Example 7

RT-PCR in ECV304 Cells Treated with Thyroid Hormone

Figure 7:
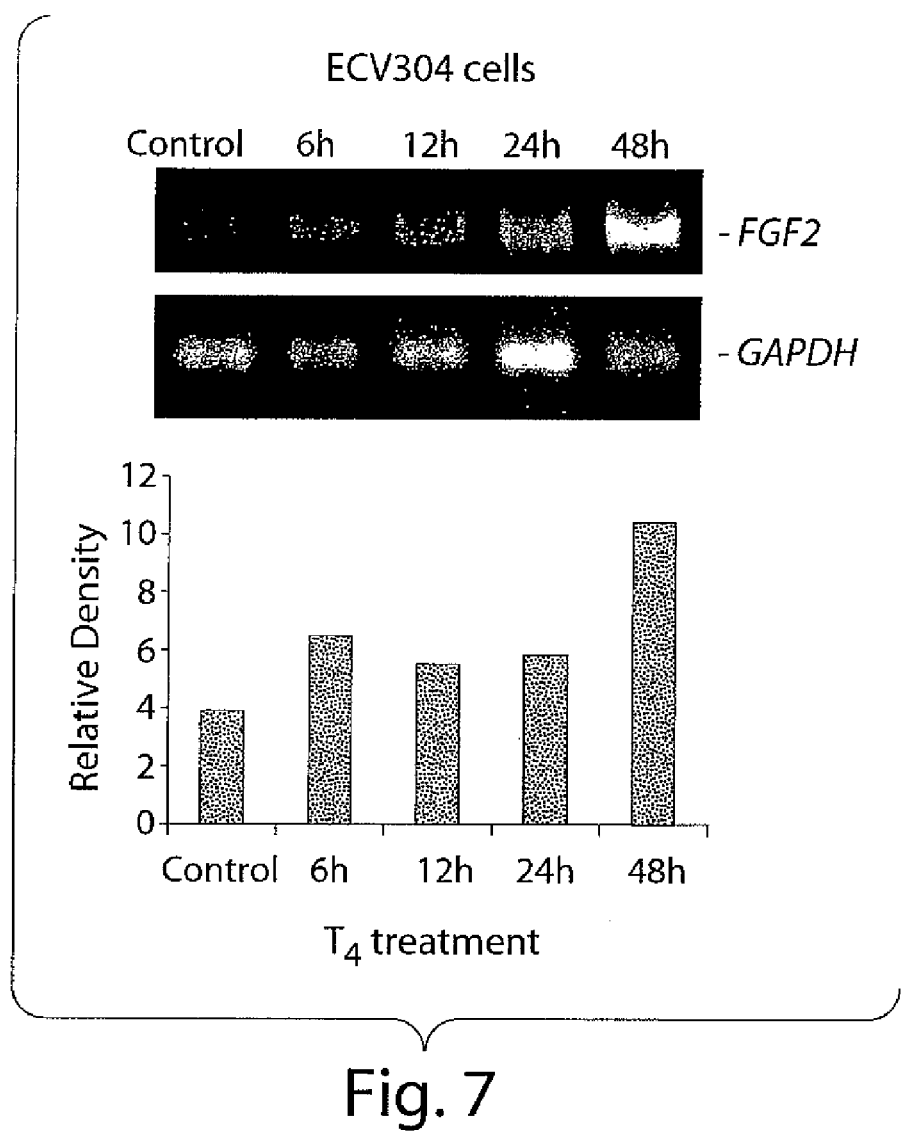
FIG. 7. T4 increases accumulation of FGF2 cDNA in ECV304 endothelial cells. Cells were treated for 6 to 48 hours with T4 ($10^{-7}$ mol/L) and FGF2 and GAPDH cDNAs isolated from each cell aliquot. The levels of FGF2 cDNA, shown in the top blot, were corrected for variations in GAPDH cDNA content, shown in the bottom blot, and the corrected levels of FGF2 are illustrated below in the graph (mean±SE of mean; n=2 experiments). There was increased abundance of FGF2 transcript in RNA extracted from cells treated with T4 at all time points. *P<0.05; **P<0.01, indicating comparison by ANOVA of values at each time point to control value.

The final question addressed in studies of the mechanism of the proangiogenic action of T4 was whether the hormone may induce FGF2 gene expression. Endothelial cells were treated with T4 ($10^{-7}$ mol/L) for 6 to 48 hours, and RT-PCR-based estimates of FGF2 and GAPDH RNA (inferred from cDNA measurements; FIG. 7) were performed. Increase in abundance of FGF2 cDNA, corrected for GAPDH content, was apparent by 6 hours of hormone treatment and was further enhanced by 48 hours.

Example 8A

Retinal Neovascularization Model in Mice (Diabetic and Non-diabetic)

To assess the pharmacologic activity of a test article on retinal neovascularization, Infant mice are exposed to a high oxygen environment for 7 days and allowed to recover, thereby stimulating the formation of new vessels on the retina. Test articles are evaluated to determine if retinal neovascularization is suppressed. The retinas are examined with hematoxylin-eosin staining and with at least one stain, which demonstrates neovascularization (usually a Selectin stain). Other stains (such as PCNA, PAS, GFAP, markers of angiogenesis, etc.) can be used. A summary of the model is below:

Animal Model

Infant mice (P7) and their dams are placed in a hyper-oxygenated environment (70-80%) for 7 days.

On P12, the mice are removed from the oxygenated environment and placed into a normal environment Mice are allowed to recover for 5-7 days.

Mice are then sacrificed and the eyes collected.

Eyes are either frozen or fixed as appropriate

The eyes are stained with appropriate histochemical stains

The eyes are stained with appropriate immunohistochemical stains

Blood, serum, or other tissues can be collected

Eyes, with special reference to microvascular alterations, are examined for any and all findings. Neovascular growth will be semi quantitatively scored. Image analysis is also available.

Example 8B

Thyroid Hormone and Diabetic Retinopathy

A protocol disclosed in J de la Cruz et al., J Pharmacol Exp Ther 280:454-459, 1997, is used for the administration of Tetrac to rats that have streptozotocin (STZ)-induced experimental diabetes and diabetic retinopathy. The endpoint is the inhibition by Tetrac of the appearance of proliferative retinopathy (angiogenesis).

Example 9

In vitro Human Epithelial and Fibroblast Wound Healing

The in vitro 2-dimensional wound healing method is as described in Mohamed S, Nadijcka D, Hanson, V. Wound healing properties of cimetidine in vitro. Drug Intell Clin Pharm 20: 973-975; 1986, incorporated herein by reference in its entirety. Additionally, a 3-dimensional wound healing method already established in our Laboratory will be utilized in this study (see below). Data show potent stimulation of wound healing by thyroid hormone.

In Vitro 3D Wound Healing Assay of Human Dermal Fibroblast Cells:

Step 1: Prepare contracted collagen gels:
1) Coat 24-well plate with 350 ul 2% BSA at RT for 2 hr,
2) 80% confluent NHDF(normal human dermal fibroblast cells, Passage 5-9) are trypsinized and neutralized with growth medium, centrifuge and wash once with PBS
3) Prepare collagen-cell mixture, mix gently and always on ice:

| Stock solution | Final Concentration |
|---|---|
| 5 × DMEC | 1 × DMEM |
| 3 mg/ml vitrogen | 2 mg/ml |
| ddH2O | optimal |
| NHDF | 2 × 10~5 cells/ml |
| FBS | 1% |

4) Aspire 2% BSA from 24 well plate, add collagen-cell mixture 350 ul/well, and incubate the plate in 37° C. CO2 incubator.
5) After 1 hr, add DMEM+5% FBS medium 0.5 ml/well, use a 10 ul tip Detach the collagen gel from the edge of each well, then incubate for 2 days. The fibroblast cells will contract the collagen gel Step 2: Prepare 3D fibrin wound clot and embed wounded collagen culture
1) Prepare fibrinogen solution (1 mg/ml) with or without testing regents.350 ul fibrinogen solution for each well in eppendorf tube.

| Stock solution | Final Concentration |
|---|---|
| 5 × DMEC | 1 × DMEM |
| Fibrinogen | 1 mg/ml |
| ddH2O | optimal |
| testing regents | optimal concentration |
| FBS | 1% or 5% |

2) Cut each contracted collagen gel from middle with scissors. Wash the gel with PBS and transfer the gel to the center of each well of 24 well plate
3) Add 1.5 ul of human thrombin (0.25 U/ul) to each tube, mix well and then add the solution around the collagen gel, the solution will polymerize in 10 mins.

After 20 mins, add DMEM+1% (or 5%) FBS with or without testing agent, 450 ul/well and incubate the plate in 37° C. CO2 incubator for up to 5 days. Take pictures on each day.

In Vivo Wound Healing in Diabetic Rats:

Using an acute incision wound model in diabetic rats, the effects of thyroid hormone analogs and its conjugated forms are tested. The rate of wound closure, breaking strength analyses and histology are performed periodically on days 3-21.

Example 10

Rodent Model of Myocardial Infarction

The coronary artery ligation model of myocardial infarction is used to investigate cardiac function in rats. The rat is initially anesthetized with xylazine and ketamine, and after appropriate anesthesia is obtained, the trachea is intubated and positive pressure ventilation is initiated. The animal is placed supine with its extremities loosely taped and a median sternotomy is performed. The heart is gently exteriorized and a 6-O suture is firmly tied around the left anterior descending coronary artery. The heart is rapidly replaced in the chest and the thoracotomy incision is closed with a 3-O purse string suture followed by skin closure with interrupted sutures or surgical clips. Animals are placed on a temperature regulated heating pad and closely observed during recovery. Supplemental oxygen and cardiopulmonary resuscitation are administered if necessary. After recovery, the rat is returned to the animal care facility. Such coronary artery ligation in the rat produces large anterior wall myocardial infarctions. The 48 hr. mortality for this procedure can be as high as 50%, and there is variability in the size of the infarct produced by this procedure. Based on these considerations, and prior experience, to obtain 16-20 rats with large infarcts so that the two models of thyroid hormone delivery discussed below can be compared, approximately 400 rats are required.

These experiments are designed to show that systemic administration of thyroid hormone either before or after coronary artery ligation leads to beneficial effects in intact animals, including the extent of hemodynamic abnormalities assessed by echocardiography and hemodynamic measurements, and reduction of infarct size. Outcome measurements are proposed at three weeks post-infarction. Although some rats may have no infarction, or only a small infarction is produced, these rats can be identified by normal echocardiograms and normal hemodynamics (LV end-diastolic pressure<8 mm Hg).

Thyroid Hormone Delivery

There are two delivery approaches. In the first, thyroid hormone is directly injected into the peri-infarct myocardium. As the demarcation between normal and ischemic myocardium is easily identified during the acute open chest occlusion, this approach provides sufficient delivery of hormone to detect angiogenic effects.

Although the first model is useful in patients undergoing coronary artery bypass surgery, and constitutes proof of principle that one local injection induces angiogenesis, a broader approach using a second model can also be used. In the second model, a catheter retrograde is placed into the left ventricle via a carotid artery in the anesthetized rat prior to inducing myocardial infarction. Alternatively, a direct needle puncture of the aorta, just above the aortic valve, is performed. The intracoronary injection of the thyroid hormone is then simulated by abruptly occluding the aorta above the origin of the coronary vessels for several seconds, thereby producing isovolumic contractions. Thyroid hormone is then injected into the left ventricle or aorta immediately after aortic constriction. The resulting isovolumic contractions propel blood down the coronary vessels perfusing the entire myocardium with thyroid hormone. This procedure can be done as many times as necessary to achieve effectiveness. The number of injections depends on the doses used and the formation of new blood vessels.

Echocardiography:

A method for obtaining 2-D and M-mode echocardiograms in unanesthetized rats has been developed. Left ventricular dimensions, function, wall thickness and wall motion can be reproducibly and reliably measured. The measurement are carried out in a blinded fashion to eliminate bias with respect to thyroid hormone administration.

Hemodynamics:

Hemodynamic measurements are used to determine the degree of left ventricular impairment. Rats are anesthetized with isoflurane. Through an incision along the right anterior neck, the right carotid artery and the right jugular vein are isolated and cannulated with a pressure transducing catheter (Millar, SPR-612, 1.2 Fr). The following measurements are then made: heart rate, systolic and diastolic BP, mean arterial pressure, left ventricular systolic and end-diastolic pressure, and + and −dP/dt. Of particular utility are measurements of left ventricular end-diastolic pressure, progressive elevation of which correlates with the degree of myocardial damage.

Infarct Size:

Rats are sacrificed for measurement of infarct size using TTC methodology.

Morphometry

Microvessel density [microvessels/mm$^2$] will be measured in the infarct area, peri-infarct area, and in the spared myocardium opposing the infarction, usually the posterior wall. From each rat, 7-10 microscopic high power fields [×400] with transversely sectioned myocytes will be digitally recorded using Image Analysis software. Microvessels will be counted by a blinded investigator. The microcirculation will be defined as vessels beyond third order arterioles with a diameter of 150 micrometers or less, supplying tissue between arterioles and venules. To correct for differences in left ventricular hypertrophy, microvessel density will be divided by LV weight corrected for body weight. Myocardium from sham operated rats will serves as controls.

Example 11

Effects of the αvβ3 Antagonists on the Pro-angiogenesis Effect of T4 or FGF2

Figures 16A, 16B:
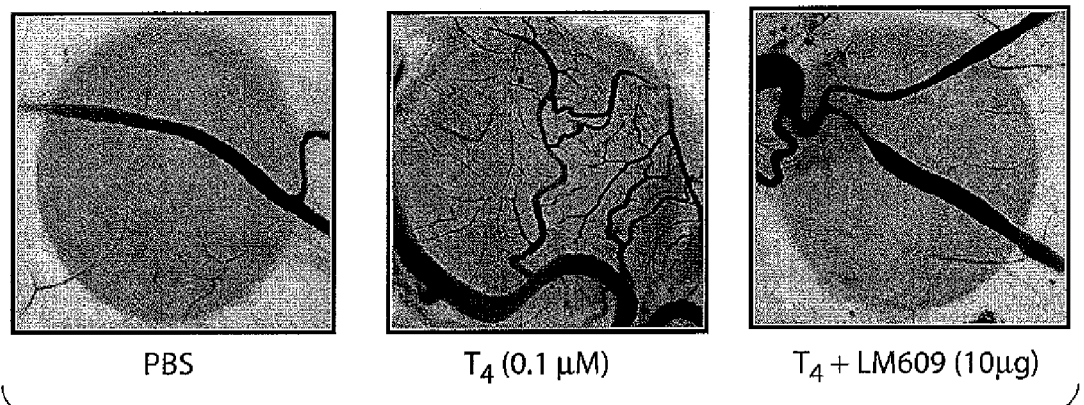
FIG. 16. Inhibitory Effect of αVβ3 mAB (LM609) on $T_4$-stimulated Angiogenesis in the CAM Model. A) Samples were exposed to PBS, $T_4$ (0.1 µM), or $T_4$ plus 10 µg/ml LM609 for 3 days. Angiogenesis stimulated by $T_4$ is substantially inhibited by the addition of the αVβ3 monoclonal antibody LM609. B) Tabulation of the mean±SEM of new branches formed from existing blood vessels during the experimental period. Data was drawn from 3 separate experiments, each containing 9 samples in each treatment group. C, D) Angiogenesis stimulated by T4 or FGF2 is also inhibited by the addition of the αVβ3 monoclonal antibody LM609 or XT 199.
Figure 16C:
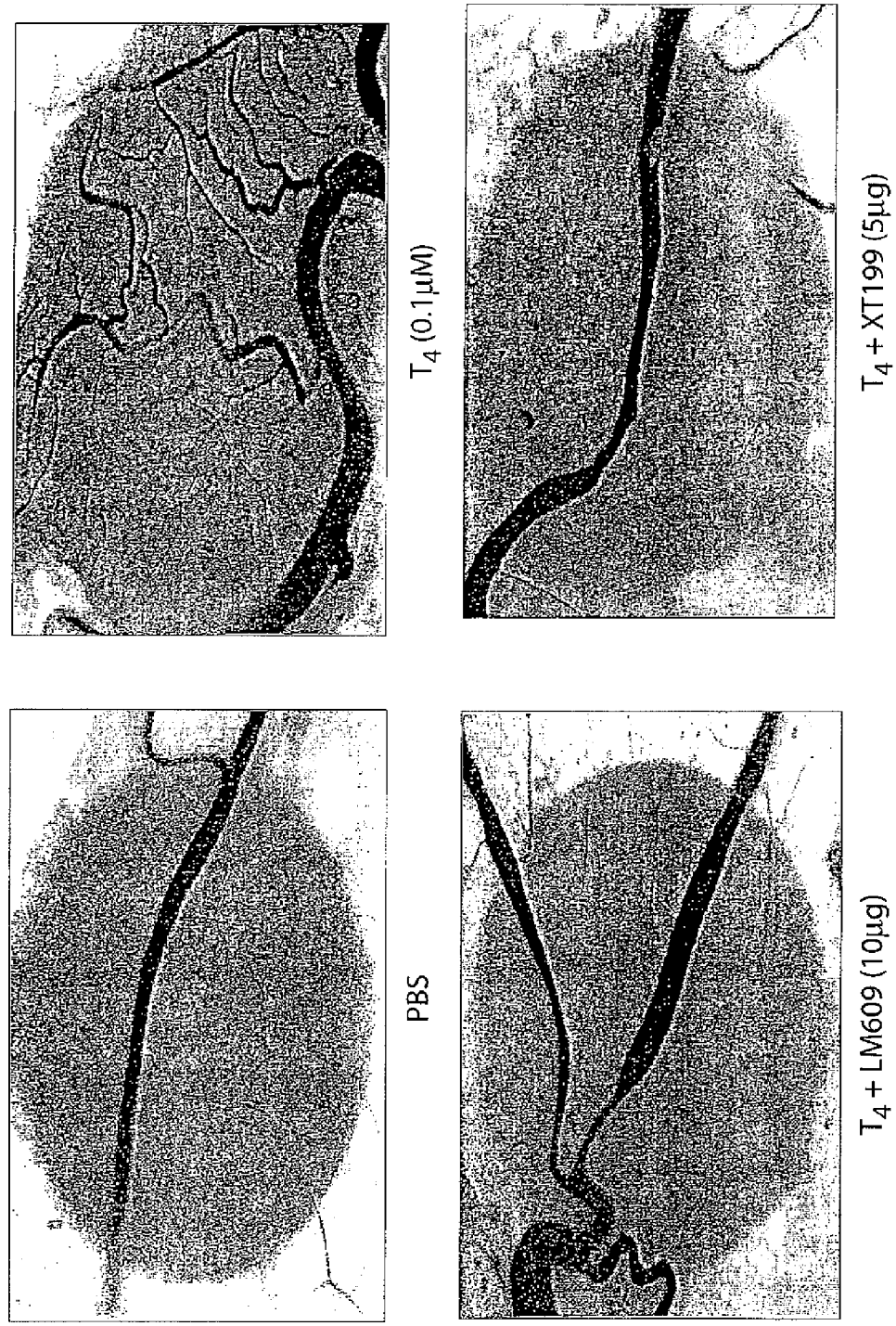

The αvβ3 inhibitor LM609 totally inhibited both FGF2 or T4-induced pro-angiogenic effects in the CAM model at 10 micrograms (FIG. 16).

Example 12

Inhibition of Cancer-Related New Blood Vessel Growth

A protocol disclosed in J. Bennett, Proc Natl Acad Sci USA 99:2211-2215, 2002, is used for the administration of tetraiodothyroacetic (Tetrac) to SCID mice that have received implants of human breast cancer cells (MCF-7). Tetrac is provided in drinking water to raise the circulating level of the hormone analog in the mouse model to 10-6 M. The endpoint is the inhibitory action of tetrac on angiogenesis about the implanted tumors.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An anti-angiogenic composition consisting of tetraiodothyroacetic acid (TETRAC), wherein said TETRAC is conjugated via a covalent bond to a copolymer of polyglycolide and polylactide, wherein said copolymer is formulated into a nanoparticle, wherein said nanoparticle is less than 200 nanometers in size, and wherein said TETRAC binds to the cell surface receptor for thyroid hormone on integrin αvβ3 at the cell membrane level and does not activate signal transduction.

2. A pharmaceutical formulation comprising the composition of claim 1 in a pharmaceutically acceptable carrier.

3. The pharmaceutical formulation of claim 2, further comprising one or more pharmaceutically acceptable excipients.

4. The pharmaceutical formulation of claim 2, wherein said formulation is formulated for parenteral, oral, rectal, or topical administration, or combinations thereof.

* * * * *